(12) United States Patent
Jones et al.

(10) Patent No.: US 11,957,356 B2
(45) Date of Patent: Apr. 16, 2024

(54) METHODS AND APPARATUS FOR STENT ASSISTED ANEURYSM COILING

(71) Applicant: NV MEDTECH, Inc., San Clemente, CA (US)

(72) Inventors: Michael Jones, Gardnerville, NV (US); Joseph Emery, Reno, NV (US)

(73) Assignee: NV MEDTECH, Inc., San Clemente, CA (US)

( * ) Notice: Subject to any disclaimer, the term of this patent is extended or adjusted under 35 U.S.C. 154(b) by 0 days.

(21) Appl. No.: 18/113,465

(22) Filed: Feb. 23, 2023

(65) Prior Publication Data

US 2023/0263527 A1 Aug. 24, 2023

Related U.S. Application Data

(60) Provisional application No. 63/313,635, filed on Feb. 24, 2022, provisional application No. 63/313,487, filed on Feb. 24, 2022.

(51) Int. Cl.
*A61B 17/12* (2006.01)

(52) U.S. Cl.
CPC .. *A61B 17/12145* (2013.01); *A61B 17/12113* (2013.01); *A61B 17/12118* (2013.01); *A61B 2017/1205* (2013.01)

(58) Field of Classification Search
CPC ........ A61B 17/12113; A61B 17/12118; A61B 17/12145
See application file for complete search history.

(56) References Cited

U.S. PATENT DOCUMENTS

| | | |
|---|---|---|
| 5,951,599 A | 9/1999 | Mccrory |
| 6,309,415 B1 | 10/2001 | Pulnev et al. |
| 6,454,780 B1 | 9/2002 | Wallace |
| 7,323,001 B2 | 1/2008 | Clubb et al. |
| 7,901,447 B2 | 3/2011 | Molaei et al. |
| 8,142,456 B2 | 3/2012 | Rosqueta et al. |
| 8,500,751 B2 | 8/2013 | Rudakov et al. |
| 8,591,568 B2 | 11/2013 | Molaei |
| 8,632,580 B2 | 1/2014 | Molaei et al. |
| 8,696,701 B2 | 4/2014 | Becking et al. |
| 8,715,340 B2 | 5/2014 | Rudakov et al. |

(Continued)

FOREIGN PATENT DOCUMENTS

| | | | |
|---|---|---|---|
| WO | 2010014447 A2 | 2/2010 | |
| WO | WO-2016210380 A1 * | 12/2016 | ............... A61F 2/90 |

(Continued)

*Primary Examiner* — Ashley L Fishback
(74) *Attorney, Agent, or Firm* — Veros Legal Solutions, LLP

(57) ABSTRACT

A device for temporarily protecting a neck of an aneurysm of a blood vessel is provided. The device includes a plurality of wires coiled to form a collapsible frame configured to expand and substantially conform to a shape of an inside surface of the blood vessel while the aneurysm is being treated. The device includes a retention wire disposed at a proximal end of the frame of the plurality of wires. The device includes a cover comprising at least a first portion configured to be disposed directly against a neck of the aneurysm while the aneurysm is being treated, the first portion having a first porosity to blood flow. Related methods of use and manufacturing are also provided.

9 Claims, 16 Drawing Sheets

(56) References Cited

U.S. PATENT DOCUMENTS

| | | |
|---|---|---|
| 8,834,559 B2 | 9/2014 | Mailander et al. |
| 8,864,815 B2 | 10/2014 | Molaei et al. |
| 8,920,430 B2 | 12/2014 | Rudakov et al. |
| 8,968,352 B2 | 3/2015 | Teoh et al. |
| 8,992,592 B2 | 3/2015 | Molaei et al. |
| 8,998,973 B2 | 4/2015 | Molaei et al. |
| 9,039,726 B2 | 5/2015 | Becking |
| 9,060,851 B2 | 6/2015 | Richter |
| 9,452,070 B2 | 9/2016 | Kusleika |
| 9,572,697 B2 | 2/2017 | Franano et al. |
| 9,572,698 B2 | 2/2017 | Franano et al. |
| 9,585,669 B2 | 3/2017 | Becking et al. |
| 9,775,730 B1 | 10/2017 | Walzman |
| 9,833,310 B2 | 12/2017 | Molaei et al. |
| 9,844,381 B2 | 12/2017 | Eckhouse et al. |
| 9,844,433 B2 | 12/2017 | Rudakov et al. |
| 10,206,798 B2 | 2/2019 | Kusleika et al. |
| 10,292,808 B2 | 5/2019 | Mangiardi et al. |
| 10,314,593 B2 | 6/2019 | Bardsley et al. |
| 10,390,934 B2 | 8/2019 | Rudakov et al. |
| 10,390,982 B1 | 8/2019 | Raychev et al. |
| 10,405,964 B2 | 9/2019 | Hannes et al. |
| 10,478,194 B2 | 11/2019 | Rhee et al. |
| 10,537,451 B2 | 1/2020 | Nicholas et al. |
| 10,632,005 B2 | 4/2020 | Gianotti et al. |
| 10,716,574 B2 | 7/2020 | Lorenzo et al. |
| 10,881,497 B2 | 1/2021 | Lorenzo et al. |
| 10,881,498 B2 | 1/2021 | Mangiardi |
| 10,893,869 B2 | 1/2021 | Choubey |
| 10,905,430 B2 | 2/2021 | Lorenzo et al. |
| 10,952,878 B2 | 3/2021 | Kusleika |
| 11,013,516 B2 | 5/2021 | Franano et al. |
| 11,033,378 B2 | 6/2021 | Rudakov et al. |
| 11,090,176 B2 | 8/2021 | Franano et al. |
| 2003/0211135 A1 | 11/2003 | Greenhalgh et al. |
| 2008/0004653 A1 | 1/2008 | Sherman et al. |
| 2008/0033341 A1 * | 2/2008 | Grad .................. A61B 18/24 604/20 |
| 2008/0119943 A1 | 5/2008 | Armstrong et al. |
| 2010/0023105 A1 | 1/2010 | Levy et al. |
| 2010/0063582 A1 | 3/2010 | Rudakov |
| 2011/0040372 A1 | 2/2011 | Hansen et al. |
| 2011/0184451 A1 | 7/2011 | Sahl et al. |
| 2013/0178891 A1 | 7/2013 | Russell et al. |
| 2013/0184810 A1 | 7/2013 | Hall et al. |
| 2013/0190856 A1 | 7/2013 | Von et al. |
| 2014/0058436 A1 * | 2/2014 | Rosenbluth ...... A61B 17/12172 606/200 |
| 2014/0058498 A1 | 2/2014 | Hannes et al. |
| 2015/0005801 A1 * | 1/2015 | Marquis ............ A61M 25/0097 606/194 |
| 2015/0190221 A1 * | 7/2015 | Schaefer .................. A61F 2/915 623/1.11 |
| 2015/0250628 A1 | 9/2015 | Monstadt et al. |
| 2016/0030050 A1 | 2/2016 | Franano et al. |
| 2017/0245862 A1 | 8/2017 | Cox et al. |
| 2018/0161185 A1 | 6/2018 | Kresslein et al. |
| 2018/0325706 A1 * | 11/2018 | Hebert ............. A61B 17/12118 |
| 2018/0333588 A1 * | 11/2018 | Lieber ............. A61B 17/12172 |
| 2019/0209178 A1 | 7/2019 | Richter et al. |
| 2019/0269411 A1 | 9/2019 | Bardsley et al. |
| 2020/0038032 A1 | 2/2020 | Rhee et al. |
| 2020/0078602 A1 | 3/2020 | Hirsh et al. |
| 2020/0138422 A1 * | 5/2020 | Hebert .................. B29D 23/00 |
| 2020/0155333 A1 | 5/2020 | Franano et al. |
| 2020/0323539 A1 | 10/2020 | Mauger et al. |
| 2020/0323620 A1 | 10/2020 | Walzman |
| 2020/0337710 A1 | 10/2020 | Lorenzo et al. |
| 2020/0360166 A1 | 11/2020 | Walzman |
| 2020/0367904 A1 | 11/2020 | Becking et al. |
| 2020/0397447 A1 | 12/2020 | Lorenzo et al. |
| 2021/0052360 A1 | 2/2021 | Jones et al. |
| 2021/0052375 A1 | 2/2021 | Jones et al. |
| 2021/0093442 A1 | 4/2021 | Lorenzo et al. |
| 2021/0137671 A1 | 5/2021 | Walzman |
| 2021/0161644 A1 | 6/2021 | Teitelbaum |
| 2021/0186675 A1 | 6/2021 | Walzman |
| 2021/0186676 A1 | 6/2021 | Walzman |
| 2021/0275187 A1 | 9/2021 | Franano et al. |

FOREIGN PATENT DOCUMENTS

| | | |
|---|---|---|
| WO | 2018109733 A2 | 6/2018 |
| WO | 2018129194 A1 | 7/2018 |
| WO | 2019175341 A1 | 9/2019 |
| WO | 2021034358 A1 | 2/2021 |

* cited by examiner

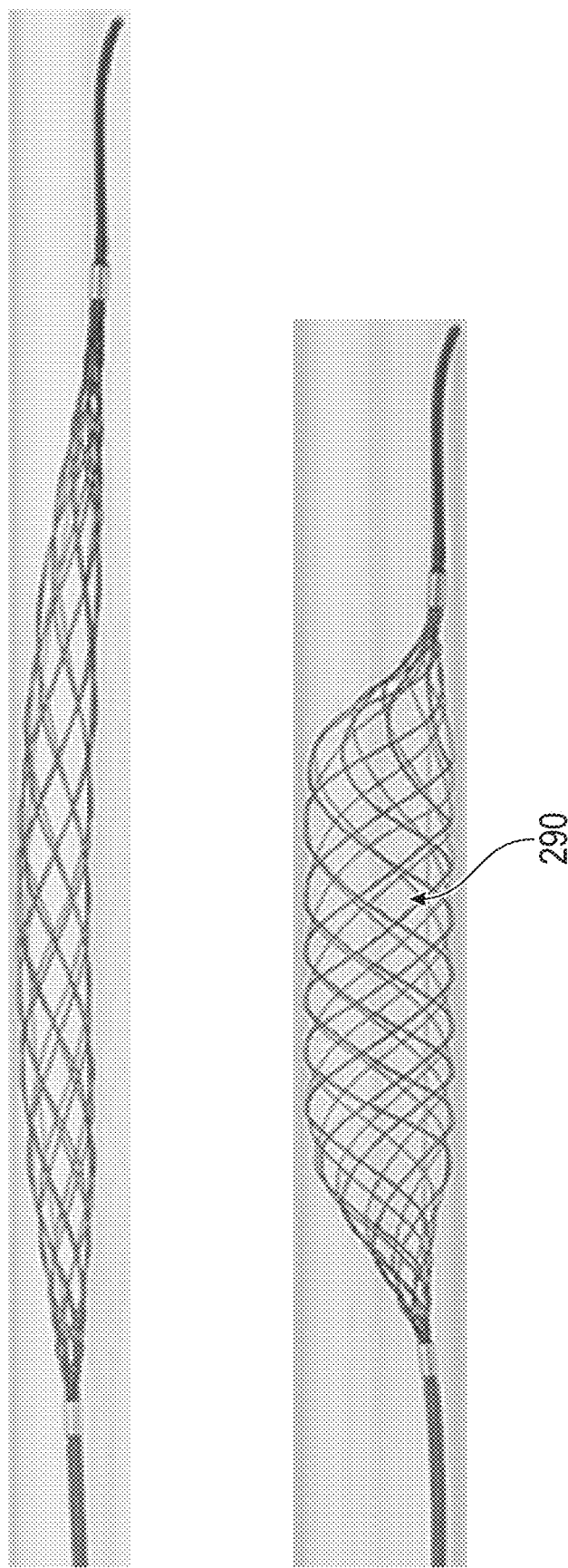

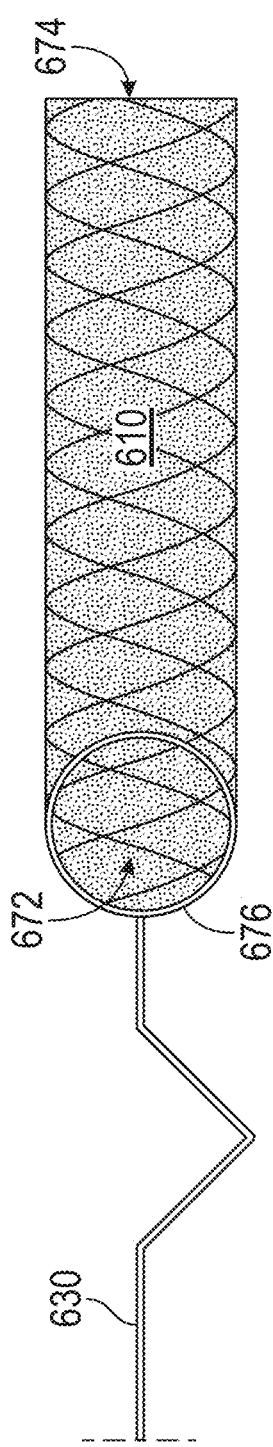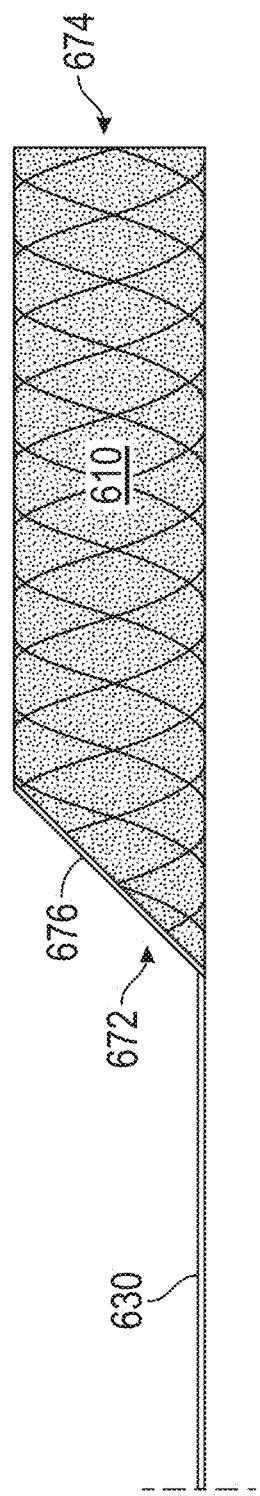

1600

1602
Coil a plurality of wires to form a collapsible frame configured to expand and substantially conform to a shape of an inside surface of the blood vessel

1604
Dispose a retention wire at a proximal end of the frame of the plurality of wires

1608
Coat each of the plurality of wires with a polymer configured to substantially reduce exposure of the plurality of wires with the blood and, thereby, substantially reduce a thrombogenicity of the coated wires compared to uncoated wires.

1606
Dispose a membrane substantially around an entire perimeter of a predetermined length of the frame, the membrane comprising at least a first portion having a first porosity to blood flow and being configured to be disposed directly against a neck of the aneurysm

1610
Form a second portion of the membrane having a second porosity to blood flow different than the first porosity of the first portion of the membrane

FIG. 13

METHODS AND APPARATUS FOR STENT ASSISTED ANEURYSM COILING

RELATED APPLICATIONS

This application claims priority to U.S. Provisional Applications 63/313,487 and 63/313,635, both filed on Feb. 24, 2022. The entire disclosures of these applications are hereby incorporated by reference in their entireties.

BACKGROUND

Intracranial aneurysms are among the most serious of medical conditions. Their typical size and location make them especially difficult to detect and treat; but even small ones, if ruptured, can cause debilitating physical and cognitive impairment, coma, and death. Initial treatment methods involved clip ligation of the neck of the aneurysm in open surgical procedures. More recently, minimally invasive endovascular techniques have been developed. Given the clinical significance of the condition and the difficulties encountered in addressing it, treatment for intracranial aneurysms remains an especially active area of device and surgical procedure development.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

In one embodiment, a device for temporarily protecting a neck of an aneurysm of an intracranial blood vessel during an aneurysm treatment. In this embodiment, the device comprises one or more wires forming a frame, wherein the frame has a collapsed configuration and an expanded configuration, wherein the frame is configured to transition in use from the collapsed configuration to a deployed configuration that substantially conforms to a shape of an inside surface of the intracranial blood vessel in the vicinity of the aneurysm being treated, and wherein the frame is configured to transition back to the collapsed configuration and removed from the intracranial blood vessel after the aneurysm is treated. The device further comprises a cover disposed on at least a portion of the frame, the cover comprising at least a first portion configured to be disposed against a neck of the aneurysm while the aneurysm is being treated, the first portion of the cover having pores formed therein defining a first porosity thereof.

In another embodiment, a device for temporarily protecting a neck of an aneurysm of an intracranial blood vessel during an aneurysm treatment. In this embodiment, the device comprises one or more wires forming a frame, wherein the frame has a collapsed configuration and an expanded configuration, wherein the frame is configured to transition in use from the collapsed configuration to a deployed configuration that substantially conforms to a shape of an inside surface of the intracranial blood vessel in the vicinity of the aneurysm being treated, and wherein the frame is configured to transition back to the collapsed configuration and removed from the intracranial blood vessel after the aneurysm is treated. In this embodiment, the device further comprises an electrospun cover disposed on at least a portion of the frame, the cover comprising at least a first portion configured to be disposed against a neck of the aneurysm while the aneurysm is being treated, the first portion of the cover having pores formed therein defining a first porosity thereof, wherein the first porosity is 20% or less, and wherein a pore size associated with the first porosity is less than approximately 10 microns.

In another embodiment, a method of treating an intracranial aneurysm is provided. In this embodiment, the method comprises threading a first microcatheter through an intracranial blood vessel and at least partly into the intracranial aneurysm, threading a guide wire through the intracranial blood vessel to a position outside a neck of the aneurysm while the first microcatheter is disposed within the intracranial blood vessel, threading a second microcatheter over the guide wire and through the intracranial blood vessel to the position outside the neck of the aneurysm, threading a device for temporarily protecting the neck of the aneurysm through the second microcatheter in a collapsed state and out of a distal end of the second microcatheter, wherein the device for temporarily protecting the neck of the aneurysm comprises one or more wires forming a collapsible frame with a cover on at least a portion thereof having pores defining a first porosity, expanding the device to a deployed configuration that substantially conforms to a shape of an inside surface of the intracranial blood vessel in the vicinity of the aneurysm with the cover defining a first porosity positioned against the neck of the aneurysm, disposing at least one coil into the aneurysm through the first microcatheter, and removing the device from the intracranial blood vessel.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

Various embodiments are discussed in detail in conjunction with the Figures described below, with an emphasis on highlighting the advantageous features. These embodiments are for illustrative purposes only and any scale that may be illustrated therein does not limit the scope of the technology disclosed. These drawings include the following figures, in which like numerals indicate like parts.

FIG. 2C illustrates a commercially available stent for stent assisted aneurysm coiling;

FIG. 4C illustrates a top view of an alternative embodiment of a temporary aneurysm neck protection device;

FIG. 4D illustrates a side view of the embodiment of FIG. C;

FIG. 13 illustrates a flowchart related to a method of manufacturing a temporary aneurysm neck protection device, in accordance with some example embodiments.

DETAILED DESCRIPTION

Figure 1A:
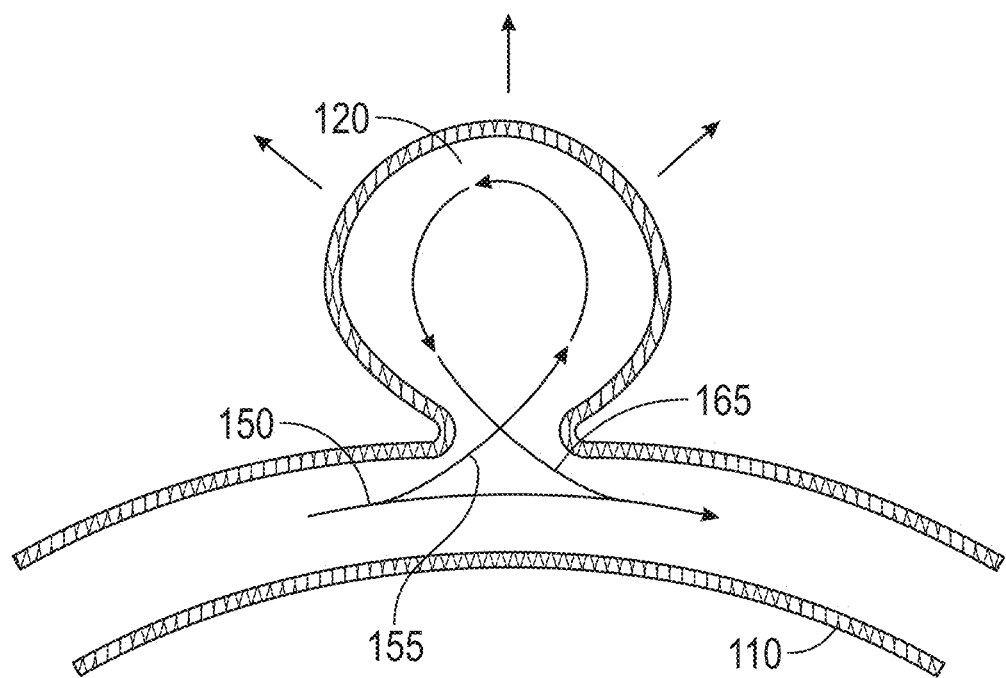
FIG. 1A illustrates blood flow in the vicinity of an aneurysm.

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

DETAILED DESCRIPTION

Collapsed Configuration—A device is in a collapsed configuration when it is sheathed proximate to and inside a distal end of a catheter ready for use in an endovascular surgical procedure.

Expanded Configuration—A device is in an expanded configuration when unsheathed outside the vasculature such that outward expansion of the sidewall is unconstrained by any surrounding walls. For flow diverters that are manually expanded by the surgeon, the expanded configuration is obtained when the flow diverter is manually expanded to its maximum intended diameter for normal use.

Deployed Configuration—A device is in the deployed configuration when unsheathed and with its side wall in contact with the inner wall of a vessel. A deployed configuration may have a smaller diameter for the sidewall than an expanded configuration depending on the size of the vessel in which the device is deployed. A device in the deployed configuration is typically close to but not fully in the expanded configuration.

Frame—One or more struts forming a structural scaffold defining a device sidewall configured to conform to the inner surface of a vessel segment when the device is in a deployed configuration. An arrangement of metal wires is a common implementation of struts for a frame.

Frame Porosity—The fractional open area of a selected portion of the sidewall defined by the struts of the device when the device is in a deployed configuration. The frame porosity may vary in different portions of a sidewall. Thus, for a given selected portion of a frame sidewall, the frame porosity is the total area of a selected portion of a sidewall minus the area of the struts defining the selected portion of the sidewall, divided by the total area of the selected portion of the sidewall when the device is in an expanded configuration.

Cover—A film or membrane connecting two or more struts of a frame and extending over some or all of the open area of the sidewall defined by the struts of the frame.

Cover Porosity—The fractional open pore area of a selected portion of a cover membrane when the device is in an expanded configuration. Cover porosity may vary in different portions of a sidewall that is covered by the membrane.

Pore Size—The size of a given pore is defined to be the diameter of an inscribed circle with three points of contact with the actual boundary of the given pore.

Cover Porosity Distribution—The cover porosity in a selected region of a cover may be distributed among groups of pores having particular pore characteristics, usually size characteristics. For example, a cover with 30% porosity may have a certain fraction of that porosity contributed by pores with a defined size range. The cover porosity distribution refers to a characterization of the amount of total porosity contributed by pores with a defined set of one or more properties.

Cover Permeability—Cover permeability is a qualitative or quantitative measure of the ability of different substances to pass through the cover when the device is in normal use in a vessel. Cover permeability is affected by several different aspects of a cover, including cover porosity and porosity distribution with respect to different size components of blood and/or particles in blood as well as the chemical properties of the cover material with respect to the chemical properties of different components of blood and/or particles in blood. Cover permeability to various blood components can also be affected by local flow and pressure conditions at the site of implantation in a vessel. The characteristics of the fluid flows encountered during use of the devices described herein where porosity and permeability are relevant device properties will be apparent from the context, and typically involve blood flow through the otherwise unobstructed ostia of intracranial blood vessels and/or necks of intracranial aneurysms over or across which the device is to be applied.

Electrospinning—A technique for depositing a layer of fibers onto a target surface. Electrospinning is expelling a jet of polymer solution from an orifice in a reservoir to the target surface under the influence of an electric field. By moving the orifice and/or the target surface during the electrospinning process, polymer fibers and fibrous polymer layers and mats having a variety of characteristics can be created. A fiber or fibrous polymer layer or mat so deposited is referred to herein as "electrospun." A variety of electrospinning techniques and materials suitable for electrospinning are described in paragraphs [0061] to [0077] of U.S. Patent Publication 2018/0161185 to Kresslein et al., which paragraphs are incorporated herein by reference.

The present disclosure relates to temporary aneurysm neck protection devices and related methods of using and/or manufacturing the same. Several example embodiments that overcome limitations of current devices will now be described in connection with one or more figures.

FIG. 1A illustrates blood flow through a vessel 110 in the region around an aneurysm 120. In many cases, especially for wider necked aneurysms, some of the vessel blood flow 150 past the aneurysm neck is diverted into the aneurysm as aneurysm inflow 155, where it may circulate backwards and then re-enter the vessel flow 150 as aneurysm outflow 165. This intrasaccular circulation pushes outward on the aneurysm wall, causing expansion and possibly rupture.

Figure 1B:
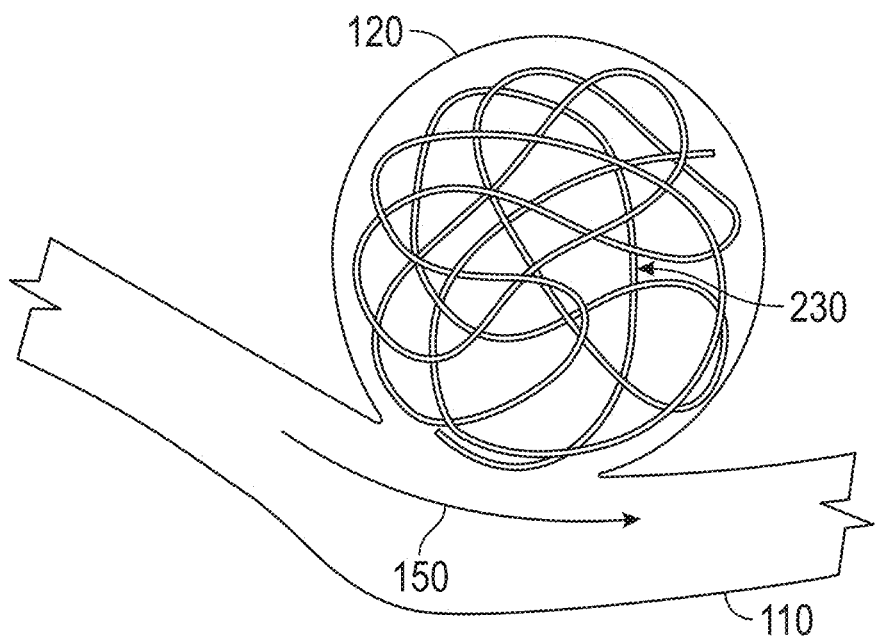
FIG. 1B illustrates a coil filled aneurysm.

In many centers, endovascular coiling is the treatment of choice for most aneurysms. This is illustrated in FIG. 1B. In this treatment protocol, one or more wire coils 230 are placed inside the aneurysm, partially or wholly filling the sac. When the aneurysm is filled with coils in this way, blood flow 150 is no longer significantly diverted into the aneurysm sac, relieving internal pressure and also assisting aneurism embolization by trapping red blood cells inside the aneurysm. Interventional neuroradiologists have developed several important adjuncts to assist in their treatment of intracranial aneurysms, such as balloon- and stent-assisted coiling of wide-necked aneurysms. These techniques have made it possible to treat many aneurysms that would have previously required more invasive open neurosurgical clipping.

Figure 2A:
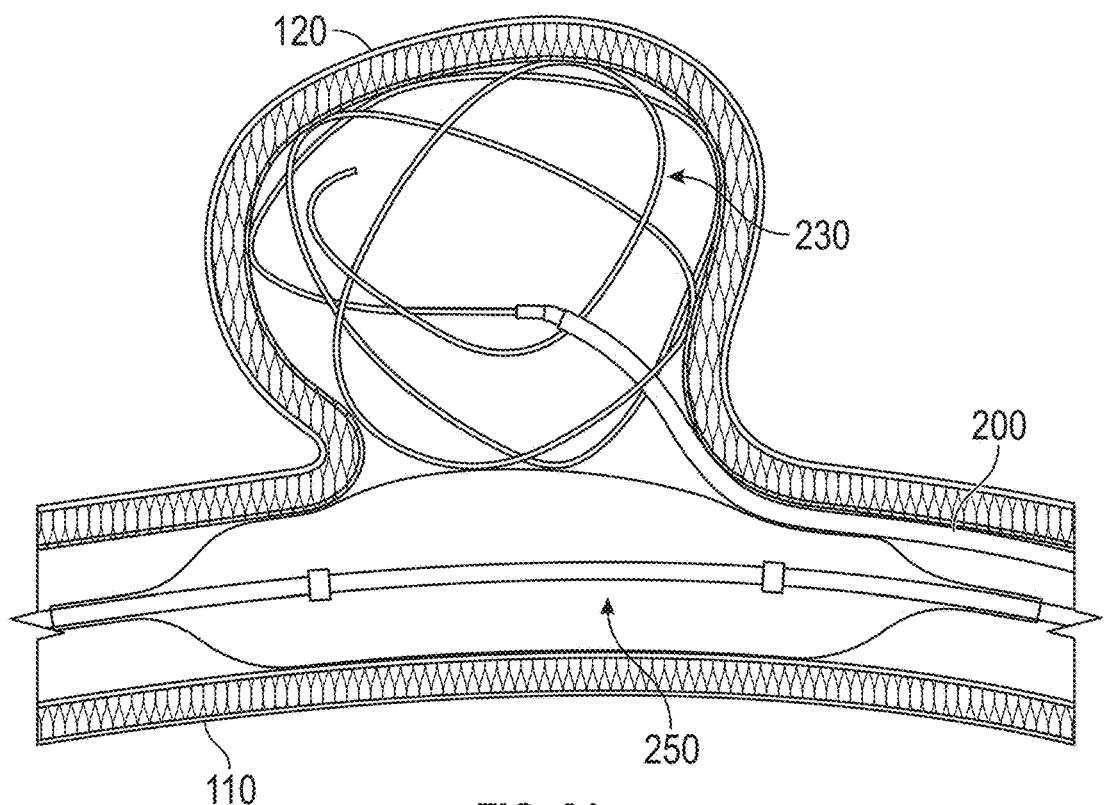
FIG. 2A illustrates balloon assisted aneurysm coiling.

FIG. 2A illustrates a portion of a blood vessel 100 having an aneurysm 120, shown as a bulging of a vessel wall in a portion of a blood vessel 110. The aneurysm 120 in FIG. 2A is being treated with balloon assisted coiling. The balloon 250 is used to confine the coil 230 as the coil 230 is deployed into the aneurysm sac.

A potential problem with balloon assisted coiling techniques is that introduction of an occlusion balloon can increase the rate of thrombus formation and thromboembolic events. In addition, presence of such a balloon in the parent vessel could theoretically promote stasis and lead to thrombus formation or platelet aggregation. Furthermore, since neurovasculature distal to the aneurysm being treated has a constant requirement for blood, occlusion balloons must be intermittently deflated during such procedures to control the limitation of blood flow to such distal neuro vasculature as well as to control blood flow into and out of the aneurysm.

Figure 2B:
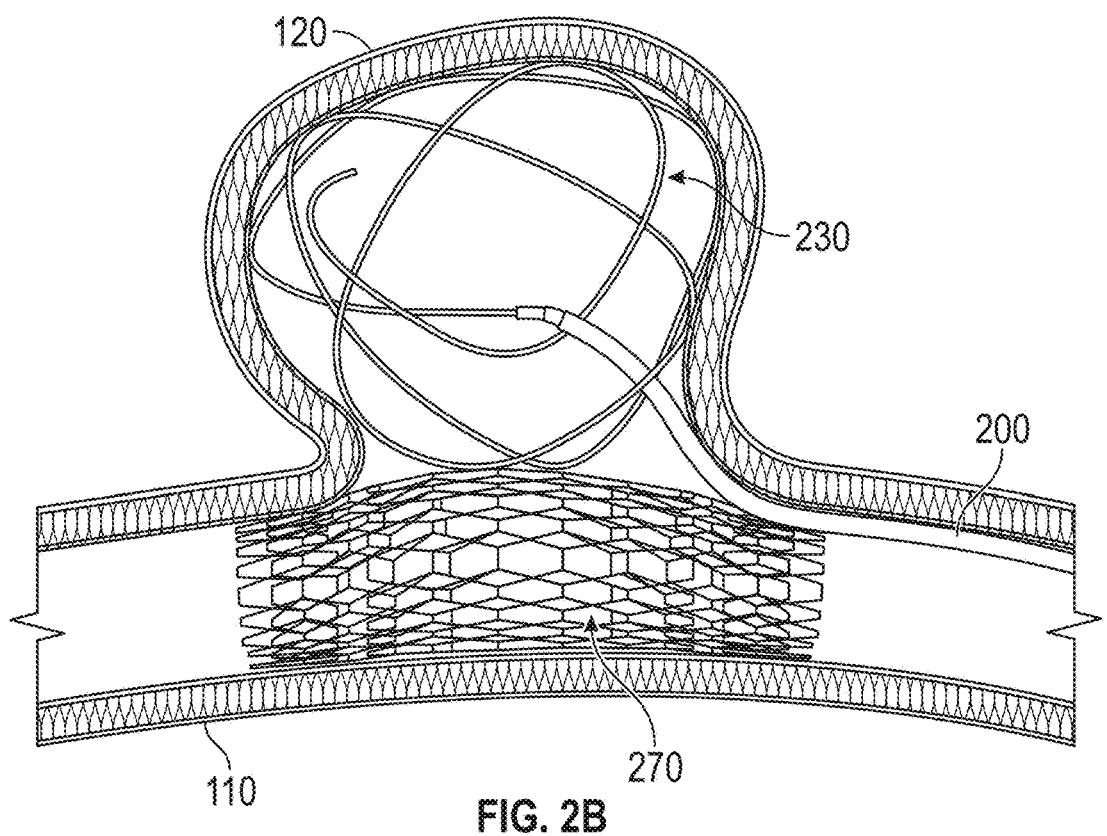
FIG. 2B illustrates stent assisted aneurysm coiling.

FIG. 2B is an illustration of stent assisted coiling. For this procedure, intravascular stents or flow diverters 270 that have been previously used as permanent implants have been modified and re-purposed for temporary coiling support. But these devices are relatively poor at protecting the neck of the aneurysm from outflow due to the high frame porosity of such conventional intravascular stents once expanded across the aneurysm neck. For example, the Comaneci aneurysm neck protection device from Rapid Medical (290, shown in FIG. 2C) is an expandable braid which opens to protect the neck and allows for coiling to proceed while "jailing" the coils within the aneurysm during the procedure. While helpful for retaining the coils, the open structure of the Comaneci device does not prevent displacement of embolic debris out of the aneurysm through the braid and, potentially, into the parent artery. Similarly, exposed metal on such devices is a known thrombogenic surface that allows clots to form on the exposed wire or wire interstices associated with the braid.

For these reasons and others, a need exists for improved temporary aneurysm neck protection devices and related methods of using and/or manufacturing the same. Accordingly, in some embodiments described herein, a device for temporarily protecting a neck of an aneurysm of a blood vessel is provided. The device may comprise one or more struts forming a frame configured to expand and substantially conform to a shape of an inside surface of the blood vessel while the aneurysm is being treated. The frame may define a frame porosity. The device may include a retention wire disposed at a proximal end of the frame of the plurality of wires for unsheathing and resheathing the device before and after an aneurysm coil insertion treatment is performed. The device may include a cover adhered to or deposited over some or all of the frame. The cover may include at least a first portion configured to be disposed directly against a neck of the aneurysm while the aneurysm is being treated. The first portion may define a cover porosity, porosity distribution, and permeability while the aneurysm is being treated. Common locations for intracranial aneurysms include the communicating arteries, the internal carotid arteries, and the middle cerebral artery. The devices described herein can, for example, be used in these arteries.

In some other embodiments, a method of utilizing a device for temporarily protecting a neck of an aneurysm of a blood vessel is provided. The method may include threading a first catheter through the blood vessel and at least partly into the aneurysm. The method may include threading a guide wire through the blood vessel to a position outside a neck of the aneurysm while the first catheter is disposed within the blood vessel and threading a second microcatheter over the guide wire and through the blood vessel to the position outside the neck of the aneurysm. The method may further include threading a device for temporarily protecting the neck of the aneurysm constructed in accordance with the principles and embodiments described herein through the second microcatheter in a collapsed state and out of a distal end of the second microcatheter such that a plurality of struts forming a collapsible frame expand and substantially conform to a shape of an inside surface of the blood vessel. A retention wire, disposed at a proximal end of the frame of the plurality of wires, may extend through the second catheter. At least a first portion of a cover over all or part of the frame may be disposed directly against a neck of the aneurysm. The first portion may define a cover porosity, porosity distribution, and permeability while the aneurysm is being treated.

In some other embodiments, a method of manufacturing a device for temporarily protecting a neck of an aneurysm of a blood vessel is provided. The method may include forming a collapsible frame configured to expand and substantially conform to a shape of an inside surface of the blood vessel. The method may include disposing a retention wire to a proximal end of the frame of the plurality of wires. The method may include disposing a cover over some or all of a predetermined length of the frame. The cover may be configured to be disposed directly against a neck of the aneurysm during an aneurysm treatment procedure such as coiling.

Several described embodiments of a temporary aneurysm neck protection device, which may be visible on angiography for precise placement, may be suitable for use in neurovascular aneurysm embolization cases, soft dilation (e.g., opening other neurovascular devices against the vessel wall), potentially vasospasm cases, and potentially vessel stenosis cases, among other suitable applications.

Some embodiments as described herein may have similar benefits to balloon assisted aneurysm coiling but without the risk of parent artery occlusion or blockage of blood flow to distal neurovasculature during expansion and/or dilation of the temporary aneurysm neck protection device. This advantageously alleviates time pressure for the clinician and may reduce the risk of parent artery thrombosis. Some embodiments as described herein may have similar benefits to stent assisted aneurism coiling but without the risk of generating or releasing embolic debris into the parent artery in association with performing the coiling treatment procedure.

Figure 3A:
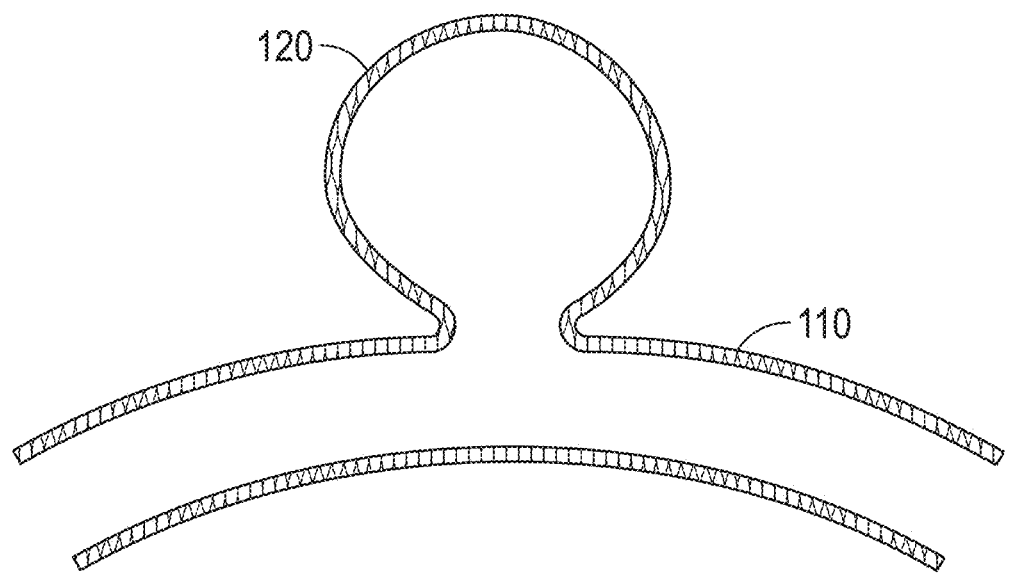
FIG. 3A illustrates a portion of a blood vessel having an aneurysm, in accordance with some embodiments.
Figure 3B:
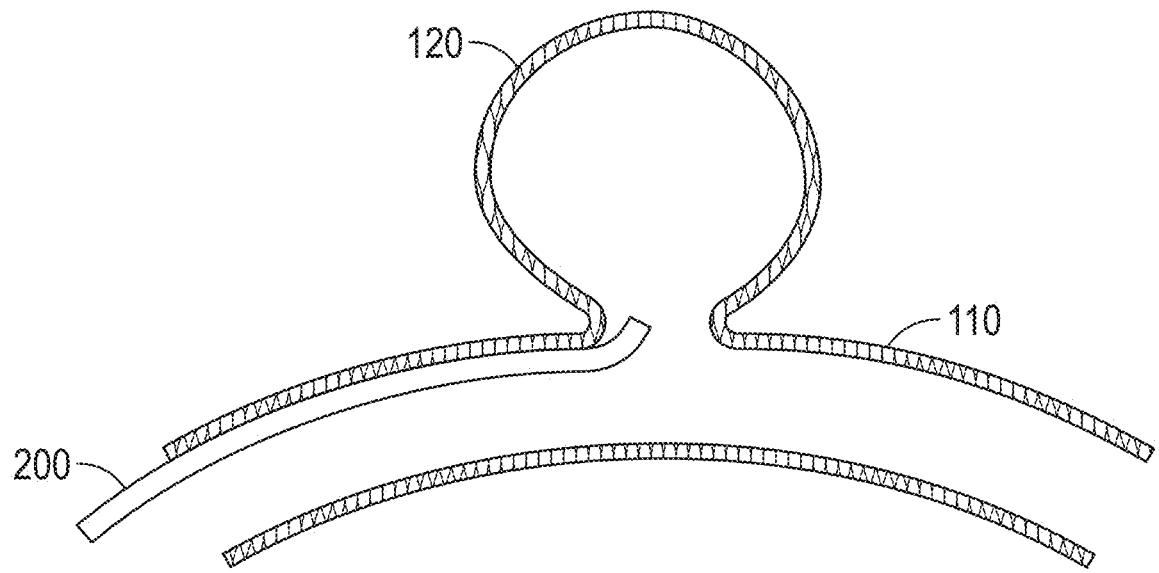
FIG. 3B illustrates a first microcatheter disposed within the blood vessel and into the aneurysm, in accordance with some embodiments.
Figure 3C:
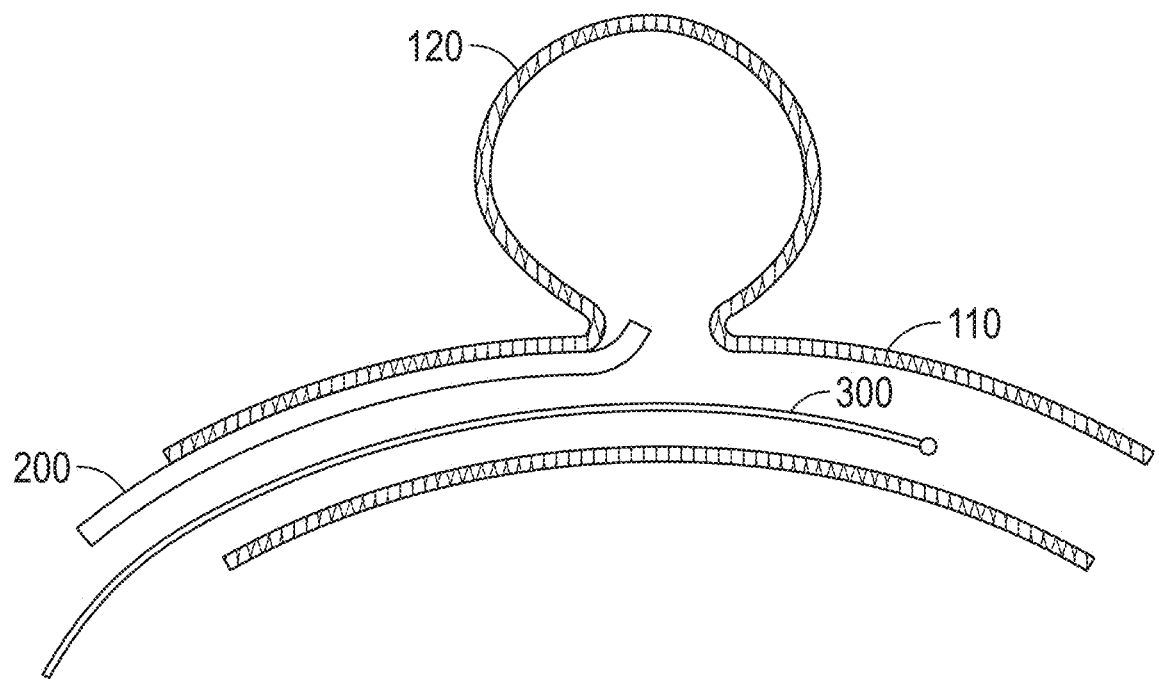
FIG. 3C illustrates a guidewire inserted into the blood vessel as illustrated in FIG. 3B, in accordance with some embodiments.
Figure 3D:
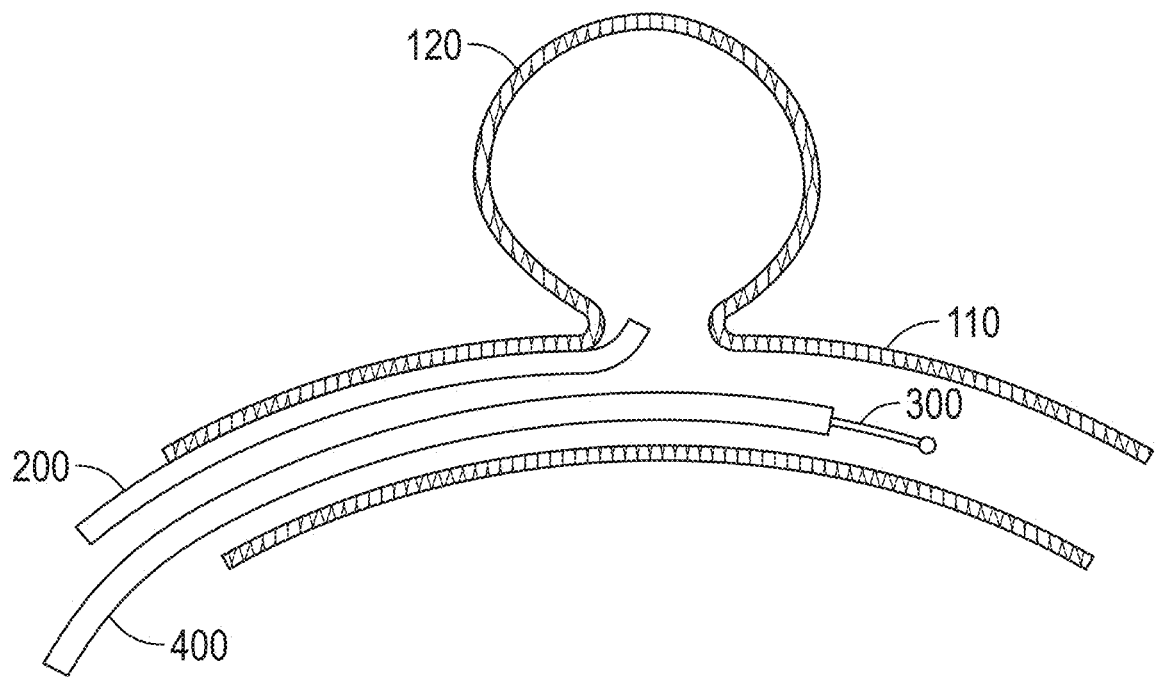
FIG. 3D illustrates a second microcatheter guided by the guide wire of FIG. 3C to be disposed within the blood vessel, in accordance with some embodiments.
Figure 3E:
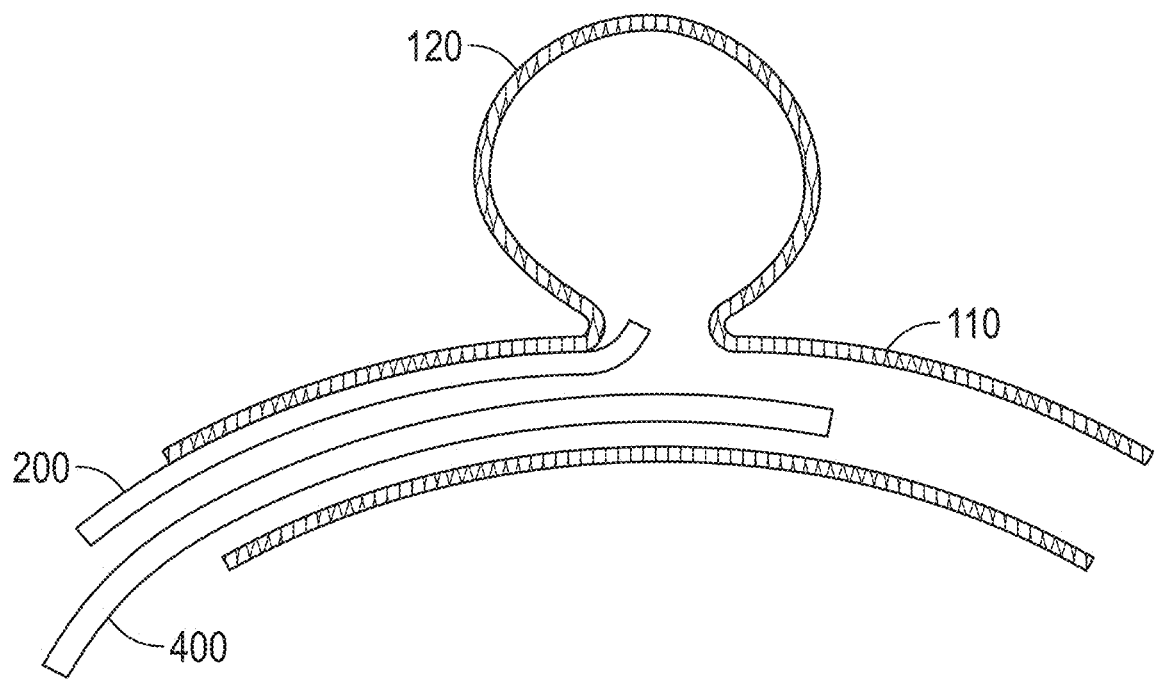
FIG. 3E illustrates the second microcatheter as illustrated in FIG. 3D, having the guide wire removed, in accordance with some embodiments.
Figure 3F:
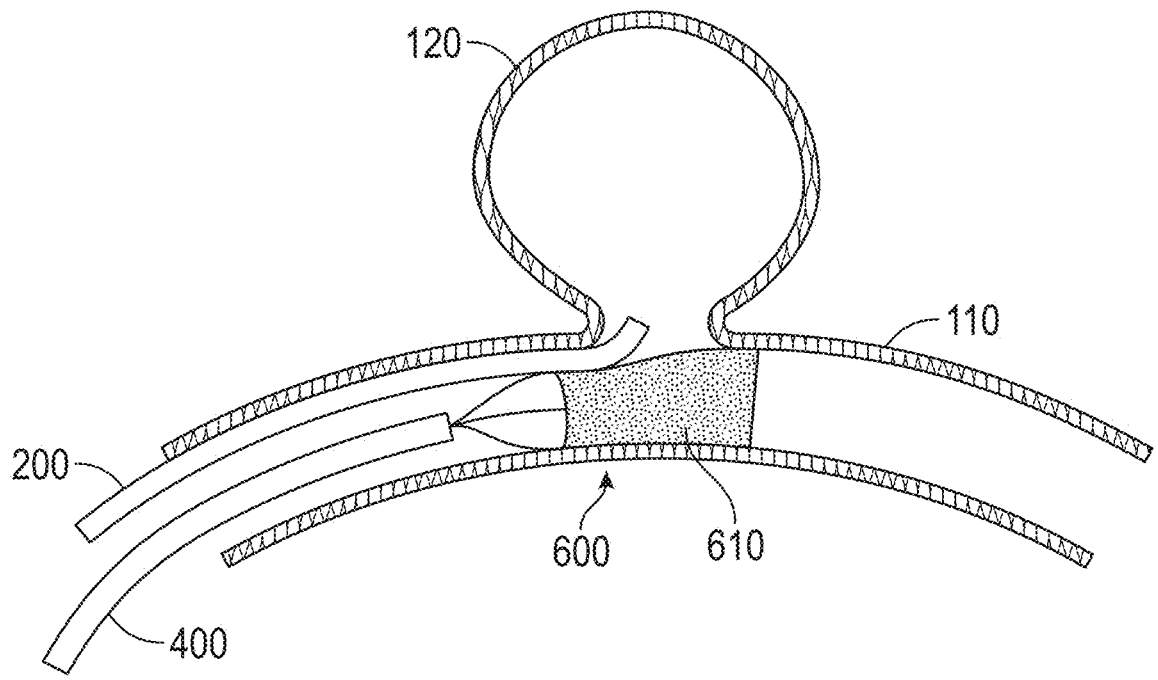
FIG. 3F illustrates a temporary aneurysm neck protection device disposed within the blood vessel and against a neck of the aneurysm, in accordance with some embodiments.

FIGS. 3A through 3F illustrate a one embodiment of performing a stent assisted aneurysm coiling procedure. As shown in FIG. 3A, a first catheter 200 may be threaded through blood vessel 110 and at least partly into aneurysm 120. First catheter 200 will be utilized to deploy coils into aneurysm 120 at a later step. As illustrated in FIG. 3B, a guide wire 300 may be threaded through blood vessel 110 to a position outside a neck of aneurysm 120. As illustrated in FIG. 3C, a second catheter 400 may be threaded through blood vessel 100, guided over guide wire 300, to a position outside a neck of aneurysm 120. As illustrated in FIG. 3D, guide wire 300 may be pulled back or removed through second catheter 400. In some embodiments, use of guide wire 300 may be optional. As illustrated in FIG. 3F, temporary aneurysm neck protection device 600 may be deployed out of a distal end of second catheter 400 over the neck of the aneurysm and a portion of the first catheter. The device 600 may self-expand under bias from the frame 610 or expand manually under surgeon control.

The stent 600 of FIG. 3F differs from conventional stents used for stent assisted coiling in that the frame of the stent comprises a cover 610, which may comprise a polymer material extending between some or all of the struts of the frame. This stent embodiment is illustrated further in FIG. 4A.

Figure 4A:
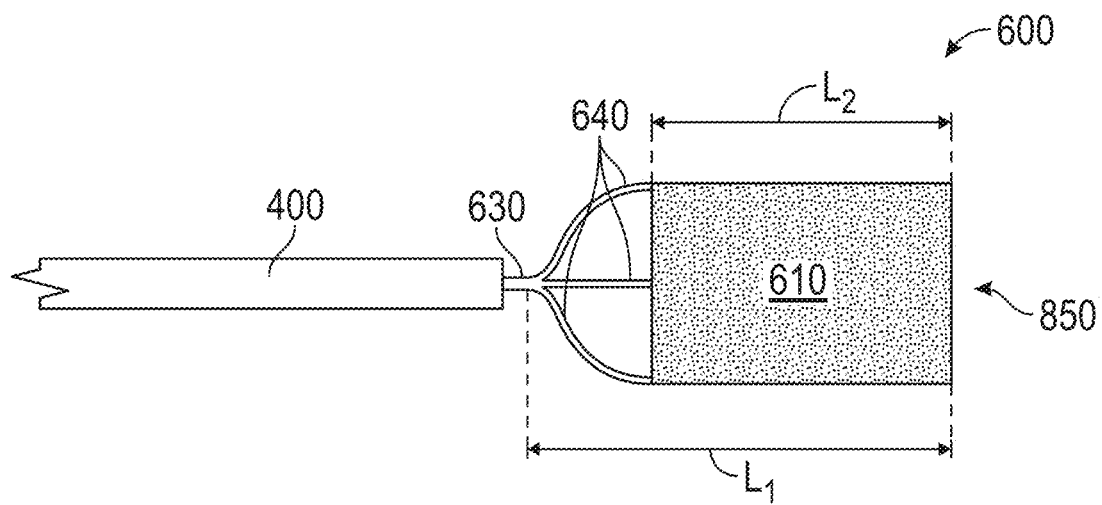
FIG. 4A illustrates a the temporary aneurysm neck protection device of FIG. 3F.
Figure 4B:
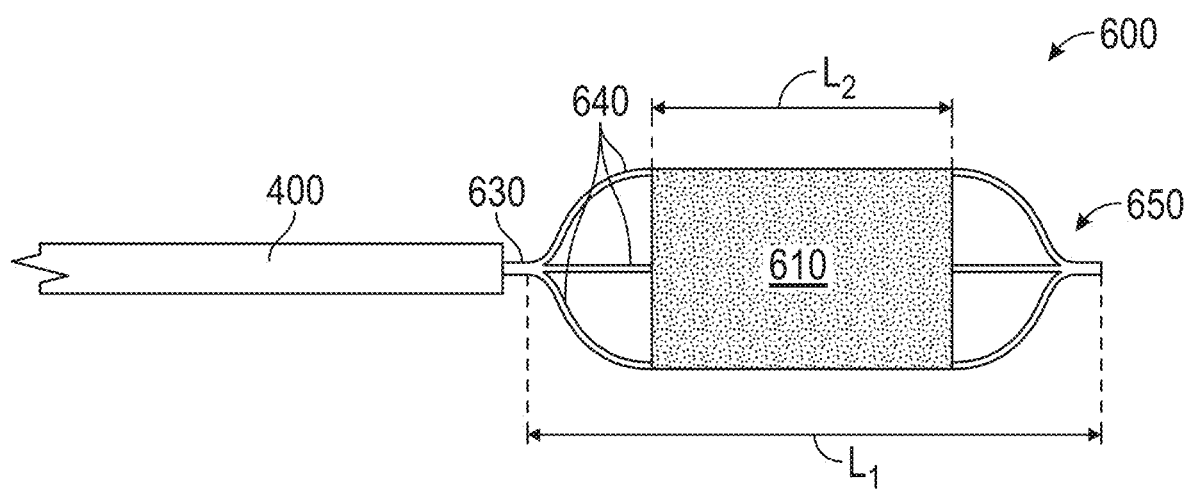
FIG. 4B illustrates a modified construction for the temporary aneurysm neck protection device of FIG. 3F with frame struts being connected at the frame distal end as well as the proximal end.

Turning now to FIG. 4A, a first embodiment of temporary aneurysm neck protection device 600 is illustrated in an expanded state. Device 600 comprises a frame defined by struts 640. FIG. 4B is a modified version of device 600 wherein the struts 640 of the frame are also connected together at the distal end of the stent in addition to the proximal end. A retention wire 630 is coupled to the frame at a proximal end of the frame. The frame may define a total stent length $L_1$ between its proximal and distal ends in the substantially expanded state. A cover 610 is disposed on some or all of the frame, in this embodiment around the circumference of the frame sidewall along a predetermined length $L_2$ (e.g., portion) of the frame of wires 640. In some embodiments, at least the portion of the frame of wires 640, over which membrane 610 is disposed, may have a substantially cylindrical sidewall. In some embodiments, distal end 850 of the frame of wires 640 may be unobstructed by any of the struts 640. The porosity and permeability of the cover 610 can be made particularly suitable for stent supported coiling treatments. The electrospinning process described above has been found advantageous for controlling cover membrane porosities and permeabilities to accomplish different clinical and surgical functions.

FIGS. 4C and 4D illustrate another embodiment of a temporary aneurysm neck protection device, wherein 4C is a top view and FIG. 4D is a side view. In this embodiment, the distal end 674 is unobstructed by any struts, similar to the embodiment of FIG. 4A. The proximal end 672 has only one location where a retention wire 630 attaches to the proximal end, leaving the opening in the proximal end 672 with little to no obstruction as well. This maximizes blood flow through the device during the coiling procedure. Also, the circumferential opening of the proximal end 672 may be angled or beveled toward the distal end from the location where the retention wire 630 attaches to the struts of the protection device. This can both increase blood flow through the device and assist re-sheathing of the device inside the introducing catheter for removal after the coiling procedure. The distal end may be heat set and bias the wire(s) towards the vessel wall.

Figure 5A:
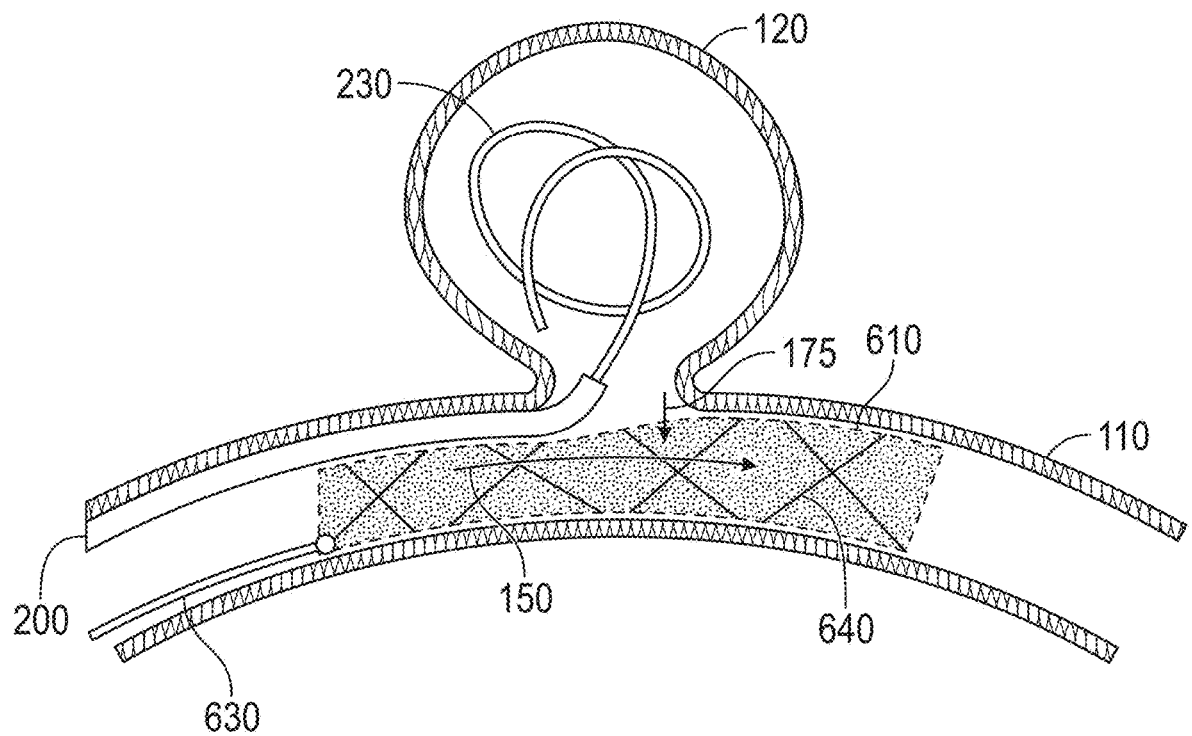
FIG. 5A illustrates blood flow during stent assisted coiling in some example embodiments.

Turning now to FIG. 5A, a temporary aneurysm protection stent 600 is shown installed across a neck of an aneurysm 120 in support of an aneurysm coiling procedure. Cover 610 is provided over the struts 640 forming the frame of the stent. The cover 610 has porosity, porosity distribution, and permeability characteristics that substantially block the circulating aneurysm inflow 155 and outflow 165 that is illustrated in FIG. 1A. It has been found that this inflow 155 and outflow blocking function can be provided with membranes of surprisingly high porosities and large pore sizes. Generally, to generate a membrane that has low permeability to inflow 155 and outflow 165 in the presence of vessel flow 150, porosity and pore size may be appropriately balanced. Higher total porosities require smaller pore sizes, while lower porosities can have large pore sizes while maintaining the desired inflow 155 and outflow 165 suppression. This may be evaluated in a more quantitative manner by considering the product of median pore size times total cover fractional porosity as a characterization of cover porosity distribution. For advantageous coiling support cover membranes, this product may be in the range of 0.1 to 50, with 5 to 20 having been found particularly suitable, if the pore size units are microns. For example, a suitable membrane may have a total porosity of 0.05 to 0.5 and a median pore size between 10 and 100 microns. In one implementation, a membrane with a porosity of 0.3 to 0.6 and a median pore size between 20 and 30 microns is utilized. In another implementation, a membrane with a total porosity between 0.05 and 0.15 and a median pore size between 30 and 100 microns is utilized. In another implementation, a membrane with a total porosity between 0.15 and 0.25 and a median pore size between 20 and 80 microns is utilized. In any of the implementations described herein, the pore size range may be from 5 to 400 microns, 5 to 200 microns, or 5 to 100 microns, wherein outliers outside of these ranges that do not significantly contribute the total porosity of the cover (e.g. less than 5% of the total porosity) are ignored.

Relatively high porosity membranes that retain the ability to block significant aneurysm inflow 155 and outflow 165 have many advantages. For example, blood components such as plasma and red blood cells can still migrate out of the aneurysm sac essentially perpendicular to the cover membrane surface (as illustrated at 175 in FIG. 5A) as the coils 230 are deployed and displace the original content of the aneurysm. Furthermore, lower pressure drops across more porous cover membranes from the blood vessel to the internal volume of the aneurysm allows blood pressure to keep the aneurism sac inflated while the coiling procedure is performed. In addition, and as explained further below, membranes with higher porosities allow the use of wire stent frames of very high porosity by providing structural support to the stent, which allows the production of highly flexible stents that are more easily navigated through complex vasculature to an aneurysm.

It may also be desired that any embolic debris generated during the coiling procedure remain trapped inside the aneurysm sac while the main blood components of plasma and red blood cells are allowed to migrate out of the aneurysm sac in a manner similar to currently used uncovered stents for coiling assist. An electrospun stent cover membrane having porosity and permeability suitable for accomplishing this is described in paragraphs [0092] through [0103] of US Published Patent Application 2021/0052360. In this embodiment, as the coils are deployed into the sac of the aneurysm, blood components displaced by the coils can migrate out as described above, but the embolic debris can be substantially retained in the sac.

Cover membranes 610 having any of the above contemplated porosity and permeability characteristics may also help to redirect coils away from the neck to effectively fill aneurysm 120 as the coil structure is built and eliminate the risk of such coils protruding into and getting caught or tangled in the frame, as has been known to occur with use of the above-described open-braid Comaneci device.

Figure 5B:
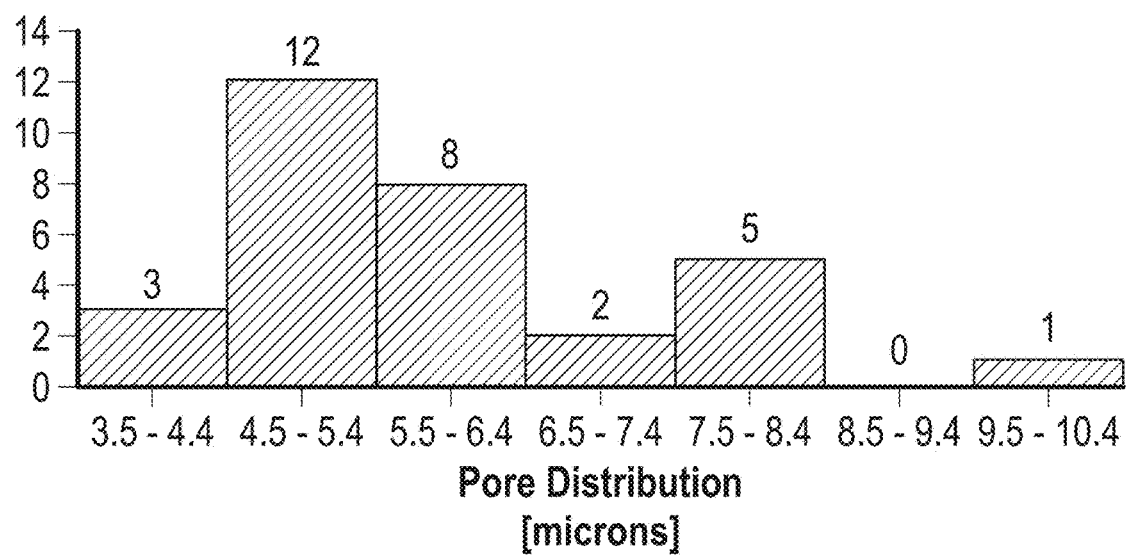
FIG. 5B is a histogram of cover pore sizes in one embodiment of a temporary aneurysm neck protection device.

In some embodiments, it may be desirable to have the cover membrane porosity be associated almost exclusively with small pores and relatively low total porosity (e.g. 10 micron and smaller median pore size and 0.2 or less fractional porosity) such that the membrane remains more permeable, (preferably significantly more permeable, e.g. at least 10% more permeable, or more preferably at least 50% more permeable) to plasma than to red blood cells. In some embodiments, the cover membrane may be substantially impermeable to red blood cell migration out of the aneurysm sac, but substantially permeable to plasma migration out of the aneurysm sac. This will still allow the sac of the aneurysm to drain fluid as the embolization coils are installed but the cover membrane will trap free red blood cells inside with the coils in addition to any embolic debris, potentially enhancing the coil driven embolization process. Another advantage of the small pore size is that radiographic contrast agent may flow through the device without entering the sac of the aneurism during the procedure. This allows fluoroscopic visualization of the coil entering the sac of the aneurysm during the procedure without interference from the contrast agent which can be focused on the vasculature. FIG. 5B is a histogram of one embodiment of pore size distribution in a portion of a cover that has been found suitable in some device embodiments. In this cover, the median pore size is between 5 and 6 microns. In this embodiment the total porosity was about 0.025. For these small pore low porosity embodiments, the covers which have been found especially suitable may be characterized by a median pore diameter times cover fractional porosity of 0.1 to 2.

Smaller pore sizes such as these can be accomplished by, for example, depositing a relatively thick multilayer mat of electrospun fibers onto the collapsible frame, essentially eliminating the ability of any large pores to span the thickness of the cover.

In some embodiments, a surgical kit may be provided for support of aneurysm sac coiling treatments where the kit contains different stents having different porosity and permeability characteristics such that the surgeon can choose the cover membrane characteristics suitable for a given procedure based on surgeon preference, experience, and the physiological characteristics of the specific aneurysm being treated.

Figure 6:
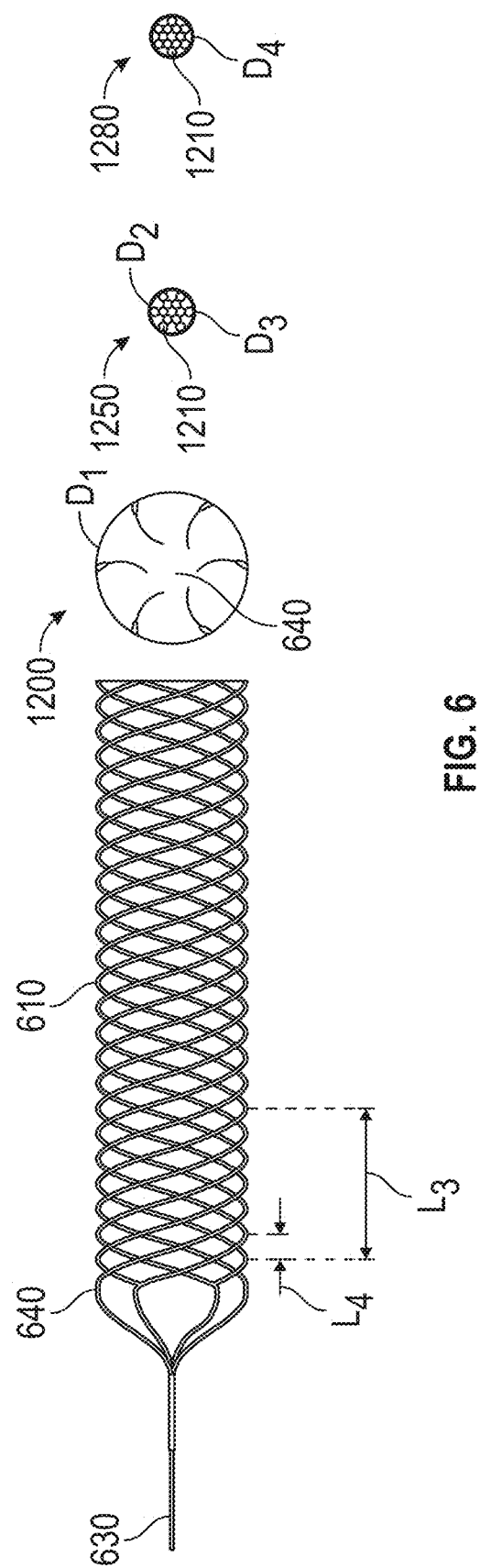
FIG. 6 illustrates side and cross-sectional views of a temporary aneurysm neck protection device in expanded and collapsed states, in accordance with some example embodiments.
Figure 7:
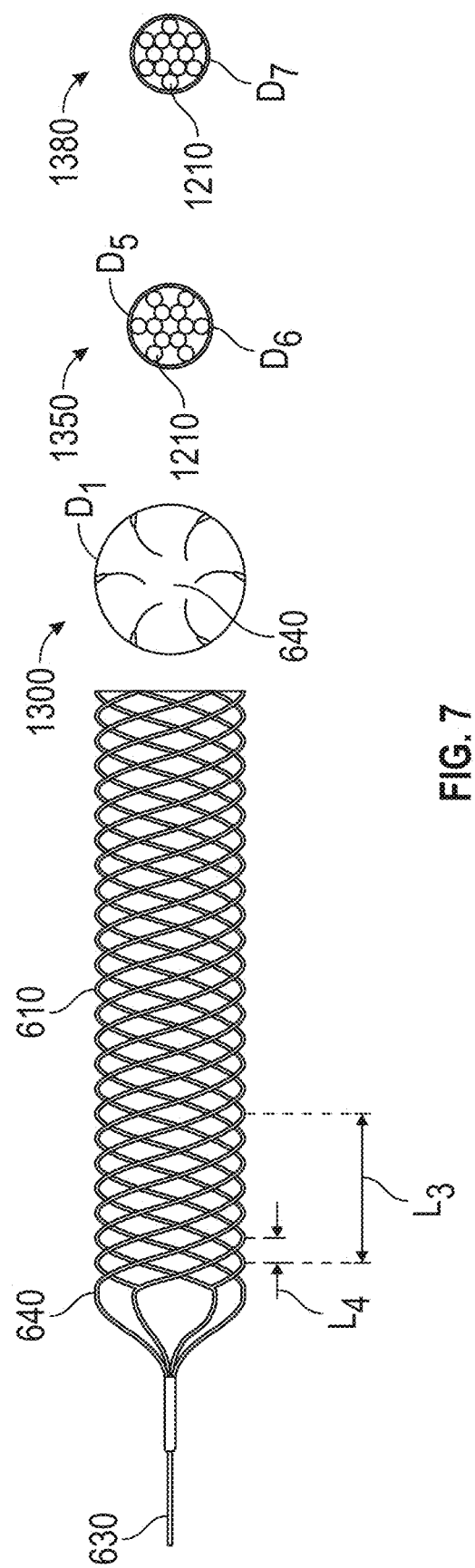
FIG. 7 illustrates side and cross-sectional views of another temporary aneurysm neck protection device in expanded and collapsed states, in accordance with some example embodiments.
Figure 8:
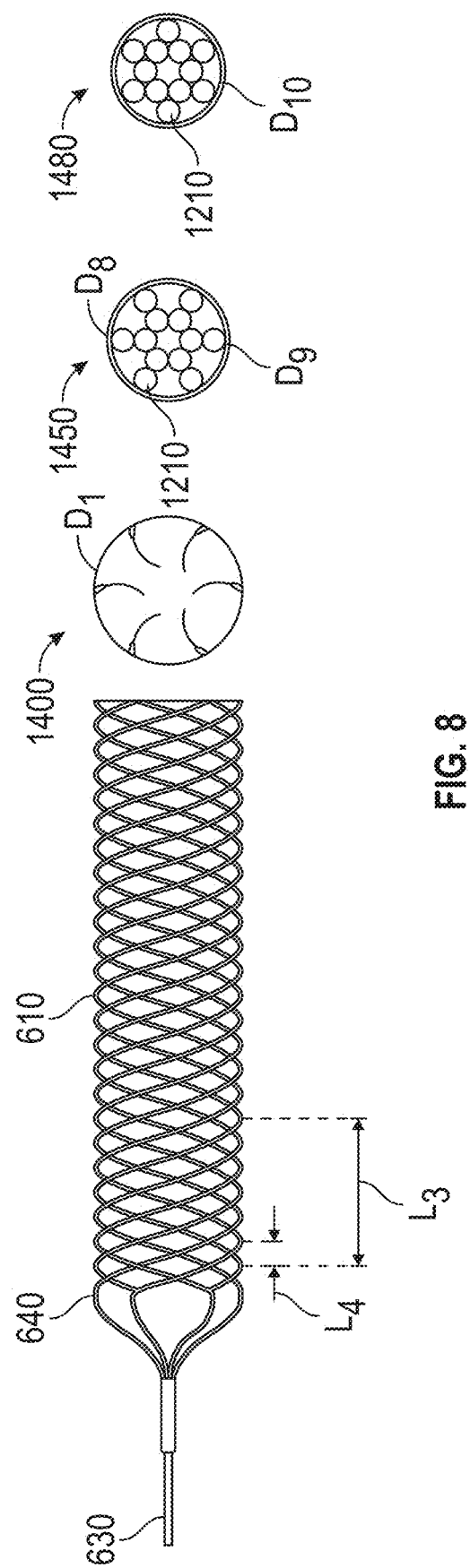
FIG. 8 illustrates side and cross-sectional views of another temporary aneurysm neck protection device in expanded and collapsed states, in accordance with some example embodiments.

As illustrated in FIGS. 6-8, the temporary aneurysm neck protection device 600 may comprise a frame comprising struts 640 formed from plurality of wires braided or coiled around one another. In some such embodiments, each of wires may be coiled into a collapsible and subsequently re-expandable, substantially helical shape or structure configured to ultimately provide the frame with its overall length $L_1$ and a diameter $D_1$ in an expanded configuration (e.g., approximately 0.12 inches or 3 mm for intracranial applications, although any other suitable maximum diameter is also contemplated).

In some such embodiments, each wire is offset from adjacent wires by a predetermined spacing $L_4$. In some embodiments, each of wires may have a predetermined pitch $L_3$ (i.e., each loop or winding of a particular one of wires extends predetermined length $L_3$ along a length of extension of temporary aneurysm neck protection device 600). In some such embodiments, the spacing $L_4$ may be determined as the result of dividing pitch $L_3$ of wires by a number of those wires wound in the same direction. The above-described geometries of wires advantageously provide for easy, unobstructed expansion and collapse of temporary aneurysm neck protection device 600 in vivo.

In some embodiments, wires 640 comprise super-elastic nitinol. In some other embodiments, a cobalt chromium may be used. In yet other embodiments, a nitinol shape memory alloy may be used. However, the present disclosure is not so limited and wires may comprise any suitably flexible, expandable and compressible material including polymers, which may themselves be electrospun polymer fibers.

In some other embodiments, a laser cut nitinol tube can be constructed, then expanded, and then heat set. The resulting nitinol tube may also be super-elastic in nature, thereby allowing its subsequent collapse for introduction into the vasculature and re-expansion during subsequent deployment.

In some embodiments, each of wires, or such an above-mentioned nitinol tube, may be coated with an elastomeric polymer 1210 configured to eliminate or substantially reduce exposed metallic surfaces of wires and, thereby, minimize thrombogenicity of the frame. The coated wires may then be covered by a membrane 610 having the desired porosity and permeability as described above.

In addition to providing the above-described selective filtering functions, membrane 610 may provide support for the underlying expanded frame of struts 640 while also possessing a very thin construction. A cover membrane 610 providing such support allows a reduction in a number of wires 640 (e.g., 6 wires as illustrated FIGS. 6-8 or fewer wires, even a single wire) needed for construction and effective operation, compared conventional devices not comprising such a membrane. The cover membrane allows an increase in frame porosity while providing all desired filtering functions with the membrane 610. In some embodiments, the frame porosity over a majority of its overall length is greater than 90%, more preferably greater than 95%.

This reduction in strut area (increase in frame porosity) also advantageously reduces device mass per unit length, delivery profile, longitudinal stiffness of, and radial force exerted by, device 600 during navigation to aneurysm 120 in the delivery system. All of these improvements separately and collectively allow for easier tracking into the vasculature and improved delivery and deployment of device(s) 600, 700. This is especially true, and advantageous, for applications to smaller and/or tortious blood vessels, such as those of the brain, where the ratio of collapsed-to-appropriately deployed radii of device(s) 600, 700 may be much smaller than for applications to larger blood vessels, such as the aorta.

In some embodiments, the primary or even sole function of the cover membrane 610 is frame support rather than filtering. In these embodiments, the frame porosity can be very high and the cover membrane porosity can also be very high and dominated by large pores that serve no substantial filtering function of any blood component, embolic debris, etc. These embodiments may still be improvements over existing coiling assist stents because they can be made especially flexible in the collapsed configuration and therefore easy for endovascular surgeons to navigate the through the tortuous intracranial vasculature to reach the aneurysm to be treated.

In one embodiment, the frame porosity is greater than 90% and the frame is covered over at least a region of its length intended for bridging an aneurism neck by an electrospun polymer membrane that is substantially permeable to blood plasma and red blood cell migration out of the aneurysm sac during coiling and substantially impermeable to blood flow past the neck of the aneurysm during normal circulation.

In another embodiment, the frame porosity is greater than 93% and the frame is covered over at least a region of its length intended for bridging an aneurism neck by an electrospun polymer membrane that is substantially permeable to blood plasma and red blood cell migration out of the aneurysm sac during coiling and substantially impermeable to blood flow past the neck of the aneurysm during normal circulation.

In another embodiment, the frame porosity is greater than 93%, the expanded configuration has a sidewall maximum diameter of less than 10 mm, and wherein the frame is covered with an electrospun membrane over at least a portion of its length having a distribution of pore sizes, wherein the distribution of pore sizes includes a first group of pores with a maximum dimension of no more than about 25 microns and a second group of pores with a maximum dimension of at least about 50 microns, and wherein the prevalence of pores in the first group is at least three times the prevalence of pores in the second group. In this embodiment, the cover porosity may be at least about 30%.

Another advantage of membrane 610 being applied to the frame of wires 640 is that the porosity, and therefore flow control, achieved by membrane 610 will advantageously allow fewer sizes of device 600 to be made available and/or used compared to existing devices, all of which have fairly narrow ranges of vessel diameters for which each size is effective at satisfactorily manipulating blood flow. For example, traditional wire braids are generally provided in 0.25 mm increments while, at least in some embodiments, temporary aneurysm neck protection device(s) 600, 700 may be made available in sizes with much larger increments, e.g., 1.0 to 1.5 mm, thereby allowing 4-6 fewer sizes of device 600 to be included in a surgical kit for aneurysm treatment.

It is also contemplated that wires may have a variety of different thicknesses, according to the requirements of a desired application. FIGS. 6-8 illustrate different example side and cross-sectional views of embodiments an example temporary aneurysm neck protection devices. The embodiments of FIGS. 6-8 are substantially similar to one another, except each utilizes wire 640 having a different diameter $D_2$, $D_5$, $D_8$ and, therefore, each illustrated embodiment also comprises respective minimum collapsed diameters for each of the two example configurations for the orientation of the wires when the frame is in the substantially collapsed state.

The first example orientation of wires in each of FIGS. 6-8, illustrated in respective cross sections 1250, 1350, 1450, comprises an innermost subset of 6 wires and an outermost subset of 6 wires. Each of the innermost threads is disposed in direct contact with each of two adjacent threads of the innermost subset and one thread of the outermost subset. A center of each of the outermost threads is radially in-line with both a center of the frame's cross section and a center of the corresponding inner thread with which the outermost thread is in direct contact.

The second example orientation of wires is shown in cross sections 1280, 1380, 1480 in each of FIGS. 6-8 and comprises the same innermost subset of 6 threads and an outermost subset of 6 threads. However, each of the innermost threads is disposed in direct contact with each of two adjacent threads of the innermost subset as well as each of two adjacent threads of the outermost subset. In this second example orientation, a center of each of the outermost threads is equally but oppositely offset from a center of each of the adjacent inner threads with which the outermost thread is in direct contact. This second example orientation is more tightly packed than the first (e.g., centers of each immediately adjacent pair of innermost threads and the center of the shared immediately adjacent outermost thread form vertices of equilateral triangles) and so provides a smallest possible minimum collapsed diameter between the two example orientations.

In FIG. 6, the wires are illustrated as having an outside diameter of approximately 0.001 inches and, accordingly, may be configured to have the maximum expanded diameter $D_1$ and a minimum contracted diameter $D_3$ (e.g., 0.005 inches) in the first example orientation of cross section 1250, and the maximum expanded diameter $D_1$ and a minimum contracted diameter $D_4$ (e.g., 0.004 inches) in the second example orientation of cross section 1280.

In FIG. 7, the wires are illustrated as having an outside diameter of approximately 0.002 inches and, accordingly, may be configured to have the maximum expanded diameter $D_1$ and a minimum contracted diameter $D_6$ (e.g., 0.010 inches) in the first example orientation of cross section 1350, and the maximum expanded diameter $D_1$ and a minimum contracted diameter $D_7$ (e.g., 0.009 inches) in the second example orientation of cross section 1280.

In FIG. 8, the wires are illustrated as having an outside diameter of approximately 0.003 inches and, accordingly, may be configured to have the maximum expanded diameter $D_1$ and a minimum contracted diameter $D_9$ (e.g., 0.015 inches) in the first example orientation of cross section 1450, and the maximum expanded diameter $D_1$ and a minimum contracted diameter $D_{10}$ (e.g., 0.013 inches) in the second example orientation of cross section 1480.

Figure 9:
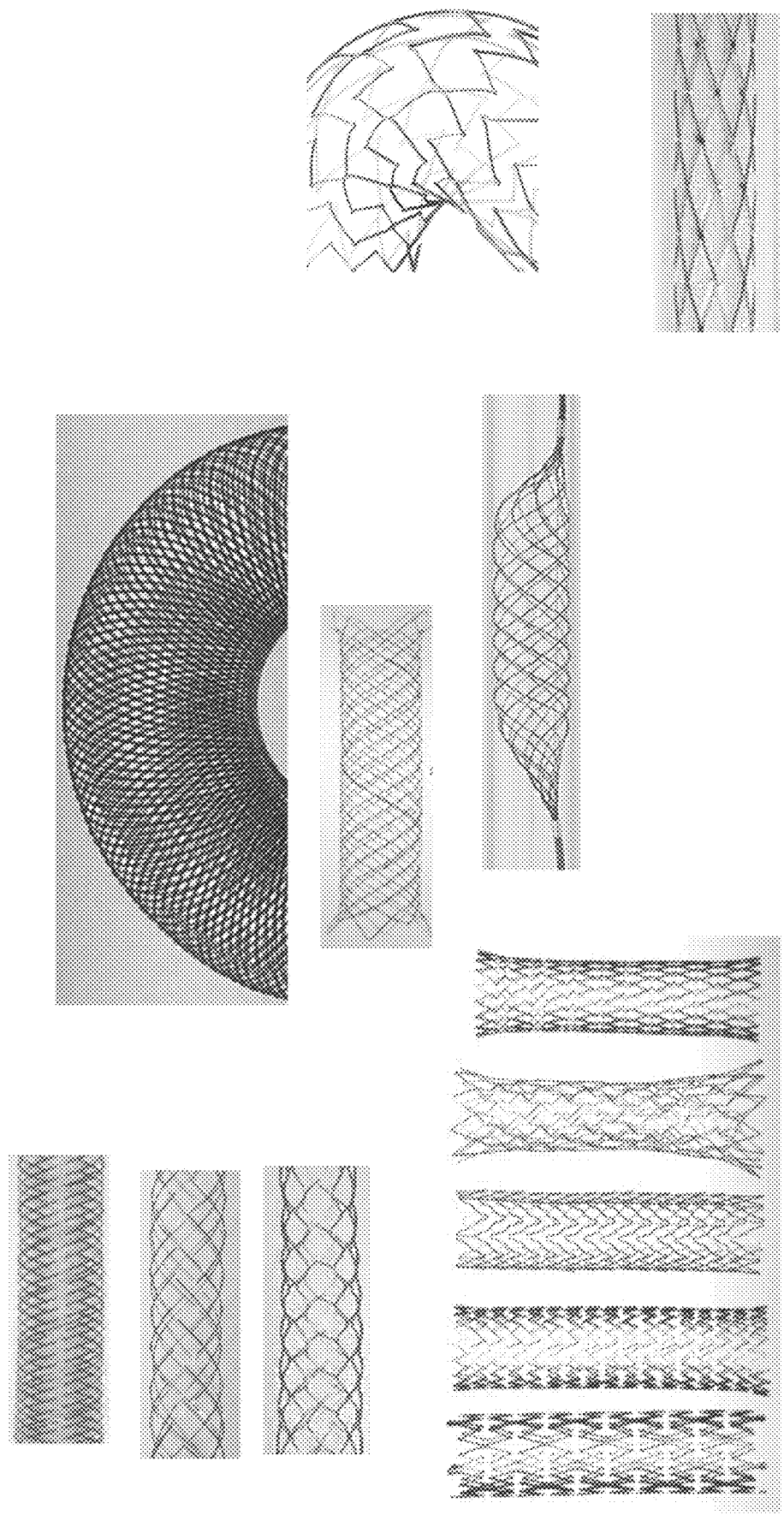
FIG. 9 illustrates example wire stent framework designs.

The specific embodiments described with reference to FIGS. 6, 7, and 8 should not be construed as limiting the frame configurations possible to be used in the inventive stent embodiments described herein. FIG. 9 shows example stent frame configurations of currently available commercial stents. As can be seen, a wide variety of frame strut configurations, strut connection schemes, coiling and braiding designs, have been developed, and more are being developed still. Any of these may be used in accordance with the inventive principles described herein to generate a novel and improved stent for aneurysm coiling support applications.

Figure 10:
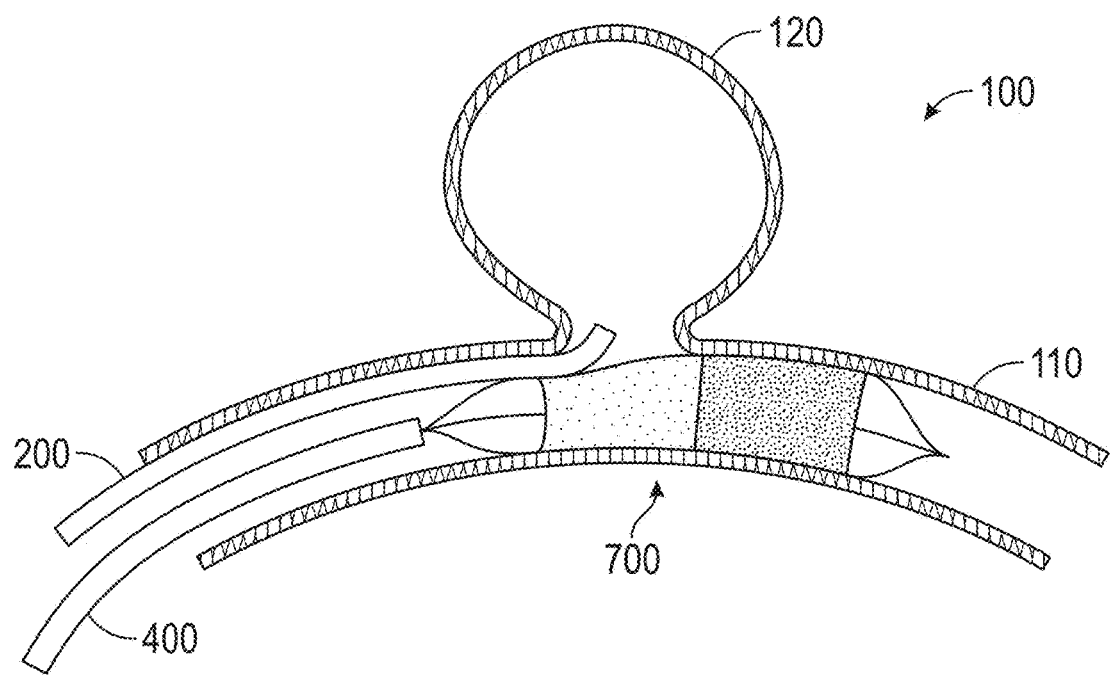
FIG. 10 illustrates yet another temporary aneurysm neck protection device disposed within the blood vessel and against a neck of the aneurysm, in accordance with some embodiments.
Figure 11:
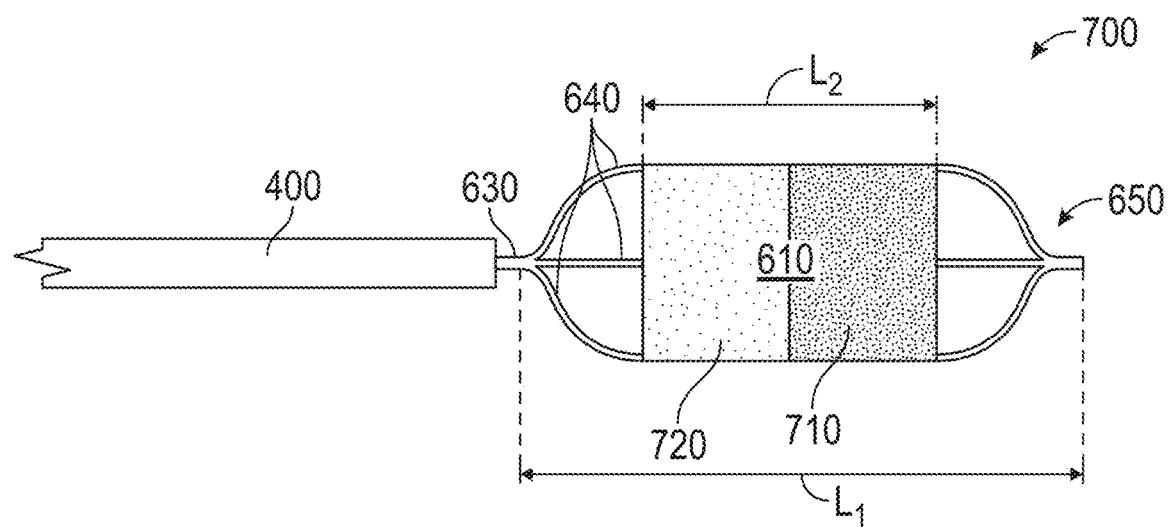
FIG. 11 illustrates a side view of at least a portion of the temporary aneurysm neck protection device of FIG. 10, in accordance with some example embodiments.

In some embodiments, the cover membrane 610 may be provided on only a portion of the deployed functional portion of the frame or may be configured to have one or more of variable porosity, variable porosity distribution, and/or variable permeability over different portions of the sidewall along its length. Embodiments having such features are illustrated in FIGS. 10 and 11. In these embodiments, the device 700 comprises a substantially cylindrical frame of wires allowing blood flow through substantially open proximal and distal ends and retention wire 630.

Membrane 610 is disposed on at least a portion of the frame and may be substantially around an entire perimeter of a predetermined length $L_2$ (e.g., portion) of frame of wires 640. However, in the embodiments of FIGS. 10 and 11, cover 610 has a first portion 710 extending along a first portion of the length of the frame and comprising first porosity and permeability characteristics, and a second portion 720 extending along a second portion of the length of the frame and comprising second porosity and/or permeability characteristics, one or both of which may be different from the first. In some embodiments where the stent is suitable for aneurysm coiling support, cover membrane portion 720 may have porosity and permeability characteristics as set forth above, and cover membrane portion 710 may be essentially fluid tight (e.g. less than 5% cover porosity). This can be accomplished by, for example, depositing a relatively thick multilayer mat of electrospun fibers onto the stent frame, essentially eliminating the ability of any pores to extend through the thickness of the cover. With this design, in the event of aneurysm 120 rupturing during a coiling procedure, retention wire 630 may be pulled and temporary aneurysm neck protection device 700 ultimately moved, relative to blood vessel 100, until the more distal, first portion 710 of membrane 610 is now disposed over the neck of aneurysm 120 to, thereby, advantageously prevent unwanted passage of the embolism or clot into the parent blood vessel 100 and prevent blood flow into the ruptured aneurysm without having to remove temporary aneurysm neck protection device 700 or insert another device.

Example Method(s) of Use

Figure 12:
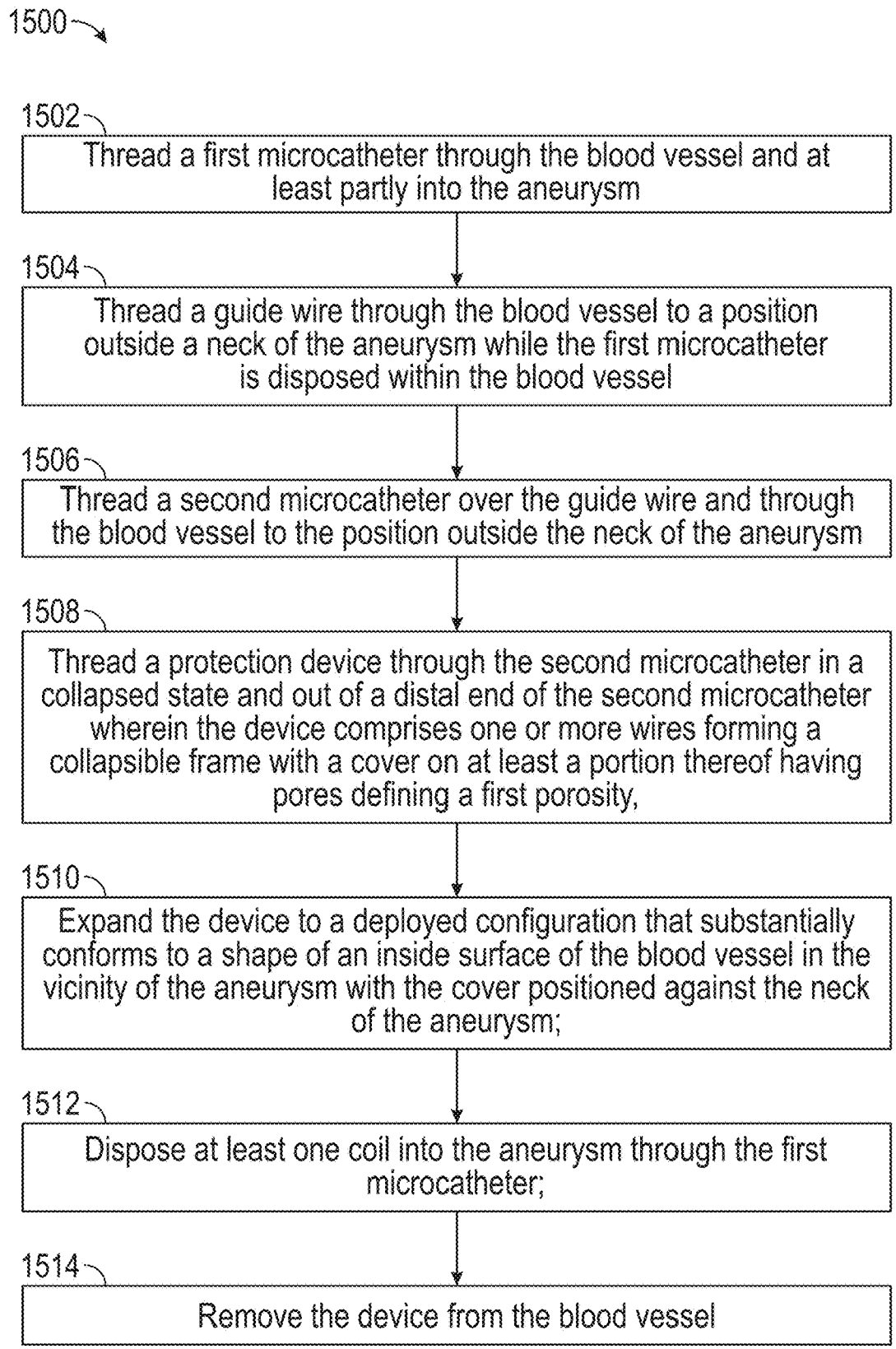
FIG. 12 illustrates a flowchart related to a method of using a temporary aneurysm neck protection device, in accordance with some example embodiments.

The disclosure now turns to FIG. 12, which illustrates a flowchart 1500 related to an example method for utilizing a device for temporarily protecting a neck of an aneurysm of a blood vessel, as described anywhere in this disclosure.

Although the method(s) disclosed herein comprise(s) one or more steps or actions for achieving the described method(s), such steps and/or actions may be interchanged with one another, and/or a subset of these steps and/or actions may be used, without departing from the scope of the claims. In other words, unless a specific order of steps or actions is specified, the order and/or use of specific steps and/or actions may be modified without departing from the scope of the claims. One or more additional steps not specifically described herein may also be included.

Step 1502 includes threading a first microcatheter through the blood vessel and at least partly into the aneurysm. For example, as previously described, first microcatheter 200 may be threaded through blood vessel 100 and at least partly into aneurysm 120.

Step 1504 includes threading a guide wire through the blood vessel to a position outside a neck of the aneurysm while the first microcatheter is disposed within the blood vessel. For example, as previously described, guide wire 300 may be threaded through blood vessel 100 to a position outside a neck of aneurysm 120 while first microcatheter 200 is disposed within blood vessel 100.

Step 1506 includes threading a second microcatheter over the guide wire and through the blood vessel to the position outside the neck of the aneurysm. For example, as previously described, second microcatheter 400 may be threaded over guide wire 300 and through blood vessel 100 to the position outside the neck of aneurysm 120.

Upon second microcatheter 400 being so disposed, guide wire 300 may be removed from second microcatheter 200 and from the blood vessel 100. In embodiments were guide wire 300 is not utilized, step 1504 may be omitted and step 1506 may comprise threading second microcatheter 400 through blood vessel 100 to the position outside the neck of aneurysm 120 without guide wire guidance.

Step 1508 includes threading the device for temporarily protecting the neck of the aneurysm through the second microcatheter in a collapsed state and out of a distal end of the second microcatheter, wherein the device comprises one or more wires forming a collapsible frame with a cover on at least a portion thereof having pores defining a first porosity. At step 1510, the device is expanded to a deployed configuration that substantially conforms to a shape of an inside surface of the blood vessel in the vicinity of the aneurysm with the cover disposed against a neck of the aneurysm.

For example, as previously described, device(s) 600, 700, for temporarily protecting the neck of aneurysm 120 may be threaded through second microcatheter 400 in a collapsed state and out of a distal end of second microcatheter 400 such that wires 640, coiled to form a collapsible frame, expand and substantially conform to a shape of an inside surface of blood vessel 100, retention wire 630, disposed at a proximal end of the frame of wires 640, extends through an entire length of second catheter 400, and at least first portion, having a first porosity to blood flow, of membrane 610 that is disposed substantially around an entire perimeter of predetermined length $L_2$ of the frame is disposed directly against a neck of aneurysm 120.

In some embodiments, a method related to flowchart 1500 may include an optional step including utilizing membrane 610 to retain an intra-aneurysmal clot within aneurysm 120 and, thereby, prevent displacement of the clot into blood vessel 100 while aneurysm 120 is being treated.

In some embodiments, a method related to flowchart 1500 may include a step 1512 including disposing at least one coil into aneurysm 120 through first microcatheter 200 while the frame of device 600, 700 is substantially conformed to the shape of the inside surface of blood vessel 100 and utilizing membrane 610 to redirect the at least one coil away from the neck of aneurysm 120 to, thereby, facilitate effective filling of aneurysm 120 with the coils. At step 1514, the device may be removed from the blood vessel.

In some embodiments, a method related to flowchart 1500 may include an optional step including utilizing membrane 610 to prevent the at least one coil from protruding into and/or tangling in wires 640 of the frame.

In some embodiments, a method related to flowchart 1500 may include an optional step including allowing blood to flow freely longitudinally through the frame and directly feed tissues distal of the aneurysm while the frame is expanded.

In some embodiments, wires 640 each converge to meet at distal end 650 of the frame. In some embodiments, none of wires 640 meet at distal end 850 of the frame, thereby providing an unobstructed distal end 850 of the frame. In some embodiments, each of wires 640 terminates, doubles back, or integrates into a substantially circular structure at distal end 850 of the frame.

In some embodiments, the frame is configured to elongate while collapsing to, thereby, minimize a collapsed diameter of device 600, 700. In some embodiments, the frame has a substantially cylindrical shape at least along the predetermined length $L_2$ on which membrane 610 is disposed. In some embodiments, the collapsible frame comprises each of wires 640 wound in a substantially helical shape, each of wires 640 comprising a plurality of helical loops and each having a predetermined pitch $L_3$. In some embodiments, each wire 640 is offset from at least one adjacent wire 640 by a predetermined spacing $L_4$. In some embodiments, there are 6 wires 640. In some embodiments, the frame is configured to self-expand under a bias from wires 640.

In some embodiments, device 600, 700 is configured to be disposed, in a collapsed state, within microcatheter 400 configured to be threaded through blood vessel 100 to a location immediately adjacent a neck of aneurysm 120. In some embodiments, device 600, 700 is configured to be threaded therethrough while microcatheter 200 is disposed in blood vessel 100 and at least a distal tip is disposed in aneurysm 120.

In some embodiments, the first porosity is within the range of approximately 0-10%, a pore size associated with the first porosity is less than approximately 20 microns, and device 600, 700 is configured to support hemostasis within aneurysm 120 by substantially blocking blood flow into aneurysm 120 through first portion 610, 710 of membrane 610. In some embodiments, the first porosity is within the range of approximately 10-40%, a pore size associated with the second porosity is greater than approximately 100 or 200 microns, and device 600, 700 is configured to allow substantially free flow of fluid through first portion of membrane 610 such that fluid freely flows out of aneurysm 120 through first portion 610 of membrane 610 as intrasacular volume is displaced by coils introduced into aneurysm 120, and systemic blood pressure keeps aneurysm 120 inflated while the coils are introduced into aneurysm 120.

In some embodiments, membrane 610 is configured to retain any intra-aneurysmal clot within aneurysm 120 and, thereby, prevent displacement of the clot into blood vessel 100 while aneurysm 120 is being treated. In some embodiments, membrane 610 is configured to redirect coils introduced into aneurysm 120 away from the neck of aneurysm 120 to, thereby, facilitate effective filling of aneurysm 120 with the coils. In some embodiments, membrane 610 is configured to prevent coils introduced into aneurysm 120 from protruding into and/or tangling in wires 640 of the frame.

In some embodiments, each end of the frame (e.g., proximal and distal) is substantially open such that the frame is configured to allow blood to flow freely longitudinally therethrough and directly feed tissues distal of the aneurysm while the frame is expanded.

In some embodiments, wires 640 form a first subset of innermost wires and a second subset of outermost wires when the frame is collapsed. In some embodiments, each of the innermost wires is disposed in direct contact with each of two adjacent innermost wires and with one of the outermost wires, and a center of each of the outermost wires is disposed in-line with a center of a cross-section of the collapsed frame and with a center of the corresponding innermost wire with which the outermost wire is in direct contact. In some embodiments, each of the innermost wires is disposed in direct contact with each of two adjacent innermost wires and with each of two adjacent outermost wires, and a center of each of the outermost wires is equally but oppositely offset from a center of each of the adjacent innermost wires with which the outermost wire is in direct contact.

In some embodiments, each of wires 640 has a diameter of one of approximately 0.001 inches, approximately 0.002 inches and 0.003 inches. In some embodiments, device(s) 600, 700 is configured to have a minimum outside diameter of one of approximately 0.004 inches, approximately 0.005 inches, approximately 0.009 inches, approximately 0.010 inches, approximately 0.013 inches, and approximately 0.015 inches when the frame is fully collapsed. In some embodiments, wherein device 600, 700 is configured to have a maximum outside diameter $D_1$ of approximately 0.12 inches or approximately 3 millimeters when the frame is fully expanded.

In some embodiments, membrane 610 further comprises second portion 720 having a second porosity to blood flow different than the first porosity of first portion 710 of membrane 610.

In some embodiments, a substantial majority of an aggregate porosity of device 600, 700 at first portion of membrane 610 is derived from the first porosity of membrane 610.

In some embodiments, each of wires 640 comprises at least one of a super-elastic nitinol, a cobalt chromium alloy, and a nitinol shape memory alloy. In some embodiments, membrane 610 comprises a polymer. In some embodiments, each of wires 640 is coated with polymer 1210 configured to substantially reduce exposure of wires 640 with the blood and, thereby, substantially reduce a thrombogenicity of the coated wires compared to uncoated wires.

Example Methods of Manufacture

The disclosure now turns to FIG. 13, which illustrates a flowchart 1600 related to an example method of manufacturing a device for temporarily protecting a neck of an aneurysm of a blood vessel, as described anywhere in this disclosure.

Although the method(s) disclosed herein comprise(s) one or more steps or actions for achieving the described method(s), such steps and/or actions may be interchanged with one another, and/or a subset of these steps and/or actions may be used, without departing from the scope of the claims. In other words, unless a specific order of steps or actions is specified, the order and/or use of specific steps and/or actions may be modified without departing from the scope of the claims. One or more additional steps not specifically described herein may also be included.

Step 1602 includes coiling (e.g. looping, braiding, joining, or otherwise arranging) a plurality of wires to form a collapsible frame configured to expand and substantially conform to a shape of an inside surface of the blood vessel. For example, as previously described, wires 640 may be coiled to form a collapsible frame configured to expand and substantially conform to a shape of an inside surface of blood vessel 100.

Step 1604 includes disposing a retention wire at a proximal end of the frame of the plurality of wires. For example, as previously described, retention wire 630 may be disposed at a proximal end of the frame of wires 640.

Step 1606 includes disposing a membrane substantially around an entire perimeter of a predetermined length of the frame, the membrane comprising at least a first portion having a first porosity to blood flow and being configured to be disposed directly against a neck of the aneurysm. For example, as previously described, membrane 610 may be disposed substantially around an entire perimeter of a predetermined length $L_2$ of the frame. Membrane 610 comprises at least a first portion 610, 720 having a first porosity to blood flow and being configured to be disposed directly against a neck of aneurysm 120.

In some embodiments, a method related to flowchart 1600 may include an optional step 1608 including coating each of the plurality of wires with a polymer configured to substantially reduce exposure of the plurality of wires with the blood and, thereby, substantially reduce a thrombogenicity of the coated wires compared to uncoated wires. For example, each wire 640 may be coated with polymer 1210 configured to substantially reduce exposure of wires 640 with the blood and, thereby, substantially reduce a thrombogenicity of the coated wires compared to uncoated wires. The dip coating can also bind the wires together at the crossing points and can provide a good bond between the electrospun membrane and the frame.

In some embodiments, a method related to flowchart 1600 may include an optional step 1610 including forming a second portion of the membrane having a second porosity to blood flow different than the first porosity of the first portion of the membrane. For example, second portion 720 of membrane 610 may be formed having a second porosity to blood flow different than the first porosity of first portion 710 of membrane 610.

In some embodiments, a method related to flowchart 1600 may include any optional step corresponding to provision, formation or assembly of any feature of any of devices 600, 700 described herein.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

What is claimed is:

1. A method of treating an intracranial aneurysm, the method comprising:

threading a first microcatheter through an intracranial blood vessel and at least partly into the intracranial aneurysm;

threading a guide wire through the intracranial blood vessel to a position outside a neck of the aneurysm while the first microcatheter is disposed within the intracranial blood vessel;

threading a second microcatheter over the guide wire and through the intracranial blood vessel to the position outside the neck of the aneurysm;

threading a device for temporarily protecting the neck of the aneurysm through the second microcatheter in a collapsed state and out of a distal end of the second microcatheter, wherein the device for temporarily protecting the neck of the aneurysm comprises one or more wires forming a collapsible frame defining a fractional frame porosity of 0.9 or greater with a cover on at least a portion thereof having pores defining a median pore size and a fractional cover porosity, wherein the median pore size is less than 10 microns, and wherein the median pore size times the fractional cover porosity is between 0.1 and 2 such that the cover is more permeable to plasma than to red blood cells and such that the cover will substantially prevent radiographic contrast agent from entering a sac of the aneurysm;

expanding the device to a deployed configuration that substantially conforms to a shape of an inside surface of the intracranial blood vessel in the vicinity of the aneurysm with the cover defining a first porosity positioned against the neck of the aneurysm;

disposing at least one coil into the aneurysm through the first microcatheter; and removing the device from the intracranial blood vessel.

2. The method of claim 1, comprising utilizing the device to retain an intra-aneurysmal clot within the aneurysm and, thereby, prevent displacement of the clot into the blood vessel while the aneurysm is being treated by the disposing.

3. The method of claim 1, comprising injecting radiographic contrast agent into the intracranial blood vessel.

4. The method of claim 1, comprising utilizing the device to prevent the at least one coil from protruding into and/or tangling in the one or more wires of the frame.

5. The method of claim 1, wherein the intracranial blood vessel has a diameter of less than 5 mm.

6. The method of claim 5, wherein the intracranial blood vessel is selected from an internal carotid artery, a communicating artery, or a middle cerebral artery.

7. The method of claim 1, wherein the cover comprises electrospun fibers.

8. The method of claim 7, wherein the frame is formed from six or fewer wires.

9. The method of claim 8, wherein the median pore size is between 5 and 6 microns.

* * * * *